(12) United States Patent
Sato et al.

(10) Patent No.: US 8,512,368 B2
(45) Date of Patent: Aug. 20, 2013

(54) PUNCTURE NEEDLE DEVICE FOR ULTRASONIC ENDOSCOPE

(75) Inventors: Masayasu Sato, Saitama (JP); Yasunobu Fujita, Saitama (JP); Tetsuya Tarumoto, Tokyo (JP)

(73) Assignee: Hoya Corporation, Tokyo (JP)

( * ) Notice: Subject to any disclaimer, the term of this patent is extended or adjusted under 35 U.S.C. 154(b) by 537 days.

(21) Appl. No.: 12/706,089

(22) Filed: Feb. 16, 2010

(65) Prior Publication Data

US 2010/0228084 A1   Sep. 9, 2010

(30) Foreign Application Priority Data

Mar. 4, 2009 (JP) ................................. 2009-050403
Apr. 23, 2009 (JP) ................................. 2009-105438
Jan. 4, 2010 (JP) ................................. 2010-000095

(51) Int. Cl.
  *A61B 17/34*   (2006.01)
(52) U.S. Cl.
  USPC ........................................ 606/185; 606/205
(58) Field of Classification Search
  USPC ................. 606/185, 205, 167, 170, 172, 181, 606/194; 600/106, 567
  See application file for complete search history.

(56) References Cited

U.S. PATENT DOCUMENTS

| | | | |
|---|---|---|---|
| 6,733,479 B1* | 5/2004 | Ott | 604/264 |
| 2001/0049496 A1* | 12/2001 | Kirchhofer et al. | 604/154 |
| 2005/0215853 A1 | 9/2005 | Ouchi | |
| 2007/0255311 A1* | 11/2007 | Hiraoka | 606/205 |
| 2007/0276180 A1* | 11/2007 | Greenburg et al. | 600/106 |

FOREIGN PATENT DOCUMENTS

| | | |
|---|---|---|
| JP | 2005-137814 | 6/2005 |
| JP | 2008-220989 | 9/2008 |

* cited by examiner

*Primary Examiner* — Ryan Severson
*Assistant Examiner* — Tin Nguyen
(74) *Attorney, Agent, or Firm* — Greenblum & Bernstein, P.L.C.

(57) ABSTRACT

A puncture needle device detachably attached to an ultrasonic endoscope via a pipe sleeve including a non-circular collar, including a cylindrical connecting body into which the pipe sleeve is inserted, the cylindrical connecting body including an insertion limit portion which contacts the pipe sleeve to prevent it from being further inserted, and a non-circular collar receiving hole engaged with the collar and irrotatable relative thereto when the pipe sleeve is inserted; a sheath projecting from the cylindrical connecting body and inserted into an internal conduit of the ultrasonic endoscope; a puncture needle inserted into the sheath; and a lock member supported by the cylindrical connecting body and movable between an unlocked position allowing the pipe sleeve to insert and remove from the cylindrical connecting body, and a locked position wherein the lock member contacts the collar of the pipe sleeve to prevent it from removing from the cylindrical connecting body.

14 Claims, 14 Drawing Sheets

PUNCTURE NEEDLE DEVICE FOR ULTRASONIC ENDOSCOPE

BACKGROUND OF THE INVENTION

1. Field of the Invention

The present invention relates to a puncture needle device for ultrasonic endoscope which is used while being inserted into an internal conduit of an ultrasonic endoscope.

2. Description of the Related Art

An ultrasonic endoscope with a pipe sleeve projecting from a control body of the ultrasonic endoscope, and a puncture needle device detachably attached to the pipe sleeve are disclosed in Japanese Unexamined Patent Publication 2005-137814.

This puncture needle device includes a cylindrical connecting body of the puncture needle device, a sheath which projects outwardly through an internal space of the cylindrical connecting body, and a puncture needle which is inserted into the sheath to be movable therein.

When the puncture needle device is used, an end of a cylindrical forceps plug, made of an elastic material such as rubber, is mounted to the pipe sleeve with the aid of the elasticity of the elastic material, and an end of the cylindrical connecting body of the puncture needle device is connected to the other end of the forceps plug with the aid of the elasticity of the forceps plug. Thereupon, the sheath (and the puncture needle) enters an internal conduit of the ultrasonic endoscope through the inside of the pipe sleeve, and the distal end of the sheath (and the distal end of the puncture needle) projects outwardly from a portion of the insertion portion of the ultrasonic endoscope in the vicinity of the distal end thereof.

In order for the operator to precisely manipulate the puncture needle device connected to the ultrasonic endoscope, tilting and rotation of the cylindrical connecting body of the puncture needle device relative to the pipe sleeve needs to be limited as much as possible.

However, in above-mentioned Japanese Unexamined Patent Publication 2005-137814, the puncture needle device tilts relative to the pipe sleeve (ultrasonic endoscope) of the ultrasonic endoscope when connected thereto via the forceps plug because the forceps plug disclosed therein is made of an elastic material.

In addition, attempts have been made to limit the rotation of the puncture needle device relative to the pipe sleeve about the central axis thereof by using frictional resistance produced between the forceps plug and each of the puncture needle device and the pipe sleeve. However, if a large torque is exerted on the puncture needle device, the puncture needle device cannot stand against this large torque solely by the aforementioned frictional resistance, thus the puncture needle device freely rotates about the central axis thereof.

SUMMARY OF THE INVENTION

The present invention provides a puncture needle device for ultrasonic endoscope, wherein tilting and rotation of the puncture needle device relative to the pipe sleeve of the ultrasonic endoscope can be limited as much as possible, even though the puncture needle device is simple in structure.

According to an aspect of the present invention, a puncture needle device is provided, detachably attached to an ultrasonic endoscope via a pipe sleeve which projects from the ultrasonic endoscope, the pipe sleeve including a non-circular-shaped collar, the puncture needle device including a cylindrical connecting body into which the pipe sleeve is inserted when the puncture needle device is attached to the ultrasonic endoscope, the cylindrical connecting body including an insertion limit portion which comes in contact with the pipe sleeve to prevent the pipe sleeve from being further inserted into the cylindrical connecting body when the pipe sleeve is inserted into the cylindrical connecting body to a predetermined position in an internal space of the cylindrical connecting body; and a non-circular-shaped collar receiving hole which is engaged with the collar and irrotatable relative to the collar when the pipe sleeve is inserted into the cylindrical connecting body to the predetermined position; a flexible sheath which projects outwardly from the cylindrical connecting body through the internal space thereof and is inserted into an internal conduit of the ultrasonic endoscope through the inside of the pipe sleeve when the pipe sleeve is inserted into the internal space of the cylindrical connecting body; a puncture needle inserted into the sheath to be movable therein; and a lock member supported by the cylindrical connecting body to be movable between an unlocked position that allows the pipe sleeve to be inserted into the cylindrical connecting body to the predetermined position and to be removed from the cylindrical connecting body, and a locked position wherein the lock member contacts the collar of the pipe sleeve, that is inserted into the cylindrical connecting body to the predetermined position, to thereby prevent the collar from moving in a removal direction from the cylindrical connecting body.

According to this structure, even though the puncture needle device is simple in structure, the puncture needle device can be totally prevented from moving relative to the pipe sleeve (ultrasonic endoscope) in the axial direction thereof if the pipe sleeve is inserted into the cylindrical connecting body to a predetermined position, in an internal space thereof, with the lock member being positioned in the unlocked position, and subsequently, the lock member is moved to the locked position.

Moreover, the puncture needle device can be totally prevented from rotating about the axis of the pipe sleeve since the non-circular-shaped collar that projects from the pipe sleeve is engaged with the collar receiving hole, which is formed on the cylindrical connecting body, so as to be irrotatable relative to the collar receiving hole.

Hence, the operator can precisely manipulate the puncture needle device connected to an ultrasonic endoscope.

Furthermore, the ultrasonic endoscope and the puncture needle device can be securely prevented from rotating relative to each other if the collar receiving hole and the collar are made to be mutually the same in shape.

In another embodiment, a puncture needle device is provided, detachably attached to an ultrasonic endoscope via a pipe sleeve which projects from the ultrasonic endoscope, the pipe sleeve including a collar, the puncture needle device including a cylindrical connecting body into which the pipe sleeve is inserted when the puncture needle device is attached to the ultrasonic endoscope, the cylindrical connecting body including an insertion limit portion which comes in contact with the pipe sleeve to prevent the pipe sleeve from being further inserted into the cylindrical connecting body when the pipe sleeve is inserted into the cylindrical connecting body to a predetermined position in an internal space of the cylindrical connecting body; and a collar receiving hole which limits a range of rotation of the collar relative to the collar receiving hole about an axis of the pipe sleeve to a predetermined rotational angle range when the pipe sleeve is inserted into the cylindrical connecting body to the predetermined position; a flexible sheath which projects outwardly from the cylindrical connecting body through the internal space thereof and is inserted into an internal conduit of the ultrasonic endoscope through the inside of the pipe sleeve when the pipe sleeve is inserted into the internal space of the cylindrical connecting body; a puncture needle inserted into the sheath to be movable therein; and a lock member supported by the cylindrical connecting body to be movable between an unlocked position that allows the pipe sleeve to be inserted into the cylindrical connecting body to the predetermined position and to be removed from the cylindrical connecting body, and a locked position at which the lock member contacts the collar on an opposite side thereof from the insertion limit portion to thereby prevent the pipe sleeve from moving in a removal direction from the cylindrical connecting body at any rotational position of said collar within the predetermined rotational angle range when the pipe sleeve is inserted into the cylindrical connecting body to the predetermined position.

According to this structure, the puncture needle device can be totally prevented from moving relative to the pipe sleeve (ultrasonic endoscope) in the axial direction thereof if the pipe sleeve is inserted into the cylindrical connecting body to a predetermined position, in an internal space thereof, with the lock member being positioned in the unlocked position, and subsequently the lock member is moved to the locked position.

Additionally, the range of rotation of the puncture needle device relative to the pipe sleeve about the axis thereof can be limited to a predetermined rotational angle by engaging the pipe sleeve into the collar receiving hole.

In this manner, the puncture needle device can be fully prevented from moving relative to the pipe sleeve in the axial direction thereof; moreover, the range of rotation of the puncture needle device relative to the pipe sleeve about the axis thereof can be limited to a predetermined range, which makes it possible for the operator to precisely manipulate the puncture needle device connected to an ultrasonic endoscope.

It is desirable for a biaser to be provided, positioned between the lock member and the cylindrical connecting body, for biasing the lock member to move toward the locked position. Accordingly, the lock member automatically moves to the locked position upon the puncture needle device being mounted to the pipe sleeve, which yields an improvement in connection operability of the puncture needle device. Moreover, the puncture needle device can be prevented from coming off the pipe sleeve when the operator (user) forgets to move the lock member to the locked position.

In addition, even in the case where an external force urging the lock member to move toward the unlocked position is unexpectedly applied to the lock member, the lock member can be held in the locked position, so that the locked state of the puncture needle device by the lock member is effectively prevented from being unexpectedly released.

It is desirable for the pipe sleeve to include a flange which projects from an outer periphery of the pipe sleeve to lie in a plane substantially orthogonal to an axis of the pipe sleeve, wherein the flange is provided closer to a body of the ultrasonic endoscope than the collar and comes into contact with the insertion limit portion when the pipe sleeve is inserted into the cylindrical connecting body to the predetermined position, and for the insertion limit portion to include a surface on the cylindrical connecting body which lies in a plane substantially orthogonal to an axis of the cylindrical connecting body. Accordingly, the cylindrical connecting body can be prevented from tilting relative to the pipe sleeve; moreover, a force preventing the cylindrical connecting body and the pipe sleeve from moving relative to each other in the axial direction of the pipe sleeve is enhanced.

It is desirable for the pipe sleeve to include a flange which projects from an outer periphery of the pipe sleeve to lie in a plane substantially orthogonal to an axis of the pipe sleeve, wherein the flange is provided closer to a body of the ultrasonic endoscope than the collar and comes into contact with the insertion limit portion when the pipe sleeve is inserted into the cylindrical connecting body to the predetermined position, and for the insertion limit portion to be an elastic member made of an elastic material. Accordingly, a clearance is not easily created between the flange of the pipe sleeve and the insertion limit portion (elastic insertion limit portion) of the cylindrical connecting body, so that the puncture needle device can be prevented from rattling relative to the pipe sleeve in an efficient manner.

It is desirable for the flange to include an annular flange, and for the cylindrical connecting body to include an annular surface with which a periphery of the annular flange comes in contact when the pipe sleeve is inserted into the cylindrical connecting body to the predetermined position. Accordingly, a force preventing the cylindrical connecting body from tilting relative to the pipe sleeve is further enhanced.

It is desirable for the lock member to include at least one control knob positioned outside the cylindrical connecting body. Accordingly, the operability of the puncture needle device is improved since the operator can easily operate the lock member while holding the control knob that is positioned outside the cylindrical connecting body.

It is desirable for the lock member to extend through the cylindrical connecting body, and for two control knobs to be fixed at opposite ends of the lock member, respectively. Accordingly, the operability of the puncture needle device is further improved.

It is desirable for a surface in the collar receiving hole to be a metal surface. Accordingly, the surface in the collar receiving hole does not easily wear (the possibility of wear is reduced) even if the pipe sleeve slides on the surface in the collar receiving hole.

It is desirable for the surface in the collar receiving hole and the pipe sleeve to be made of a same metallic material. Accordingly, the abrasion resistance of the surface in the collar receiving hole can further be improved, and hence, further reducing the possibility of wear.

It is desirable for the biaser to include at least one compression spring.

It is desirable for the elastic member to be an elastic washer.

It is desirable for the shape of the collar to be defined by a circular collar having radially opposite ends thereof cut off.

The present disclosure relates to subject matter contained in Japanese Patent Application Nos. 2009-050403 (filed on Mar. 4, 2009), 2009-105438 (filed on Apr. 23, 2009), and 2010-000095 (filed on Jan. 4, 2010) which are expressly incorporated herein by reference in their entireties.

BRIEF DESCRIPTION OF THE DRAWINGS

The present invention will be described below in detail with reference to the accompanying drawings in which.

DESCRIPTION OF THE PREFERRED EMBODIMENTS

Figure 1:
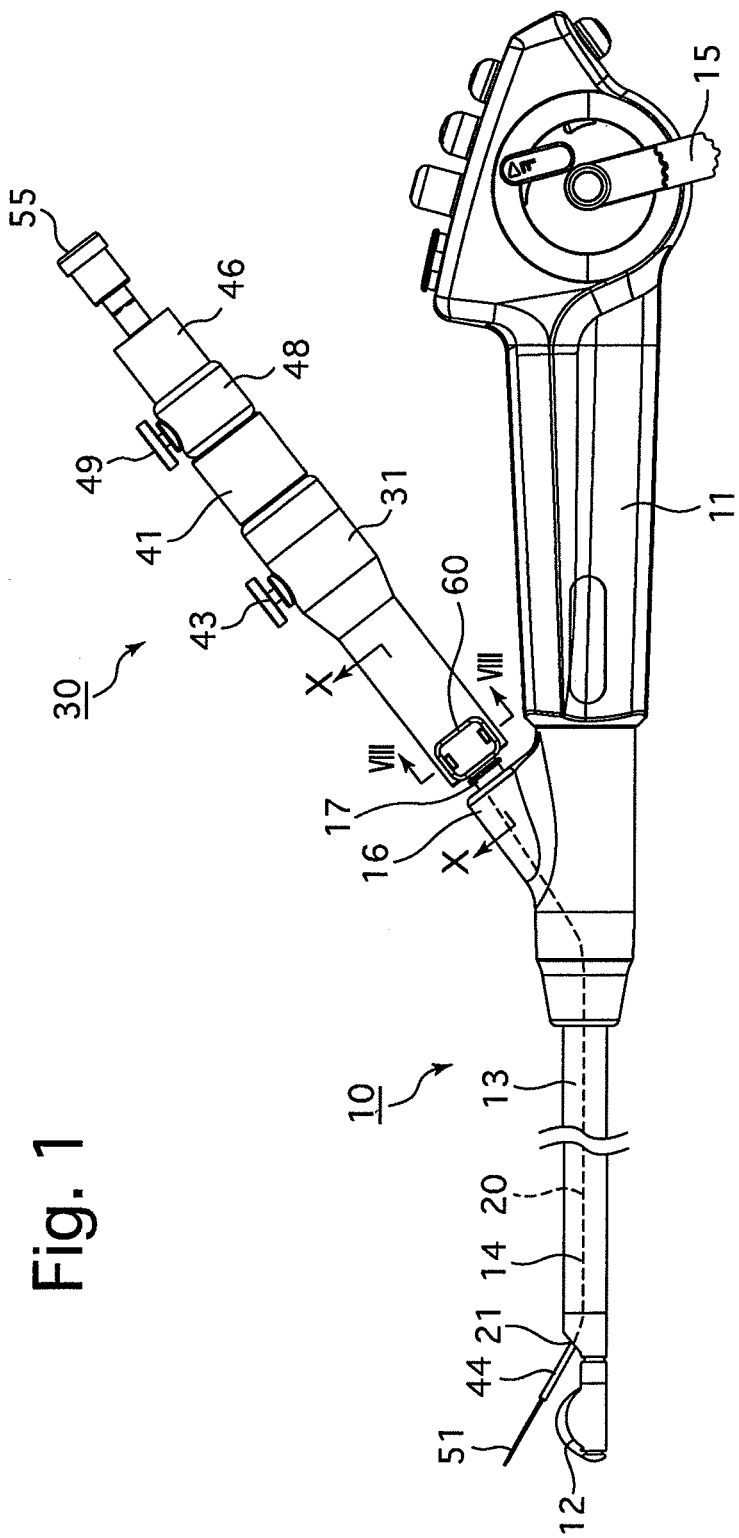
FIG. 1 is a side elevational view of a first embodiment of an ultrasonic endoscope and a puncture needle device according to the present invention, showing a state where the puncture needle device is connected to the ultrasonic endoscope with the control portion of the puncture needle device being fully contracted.
Figure 2:
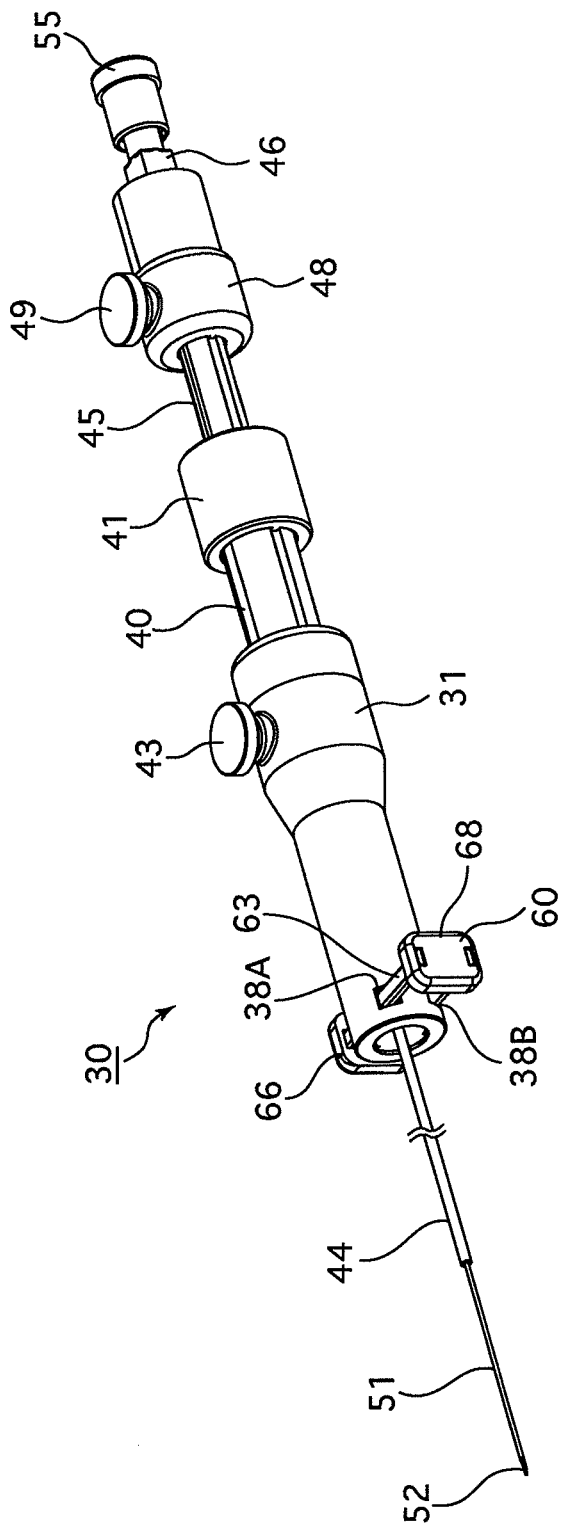
FIG. 2 is a perspective view of the puncture needle device in a state where the control portion thereof is extended from the fully-contracted state.

A first embodiment of a puncture needle device for ultrasonic endoscope according to the present invention will be hereinafter discussed with reference to FIGS. 1 through 11. In the following descriptions, the distal-end side of an insertion portion 13 is defined as the front side of an ultrasonic endoscope 10 and a control body 11 side is defined as the rear side of an ultrasonic endoscope 10. Additionally, in a puncture needle device 30, the tip of a puncture needle (centesis needle) 51 is defined as the front side of the puncture needle device 30 and a stylet support cap 55 side is defined as the rear side of the puncture needle device 30.

Firstly, the structure of the ultrasonic endoscope 10 to which the puncture needle device 30 can be detachably attached will be discussed hereinafter.

Figure 3:
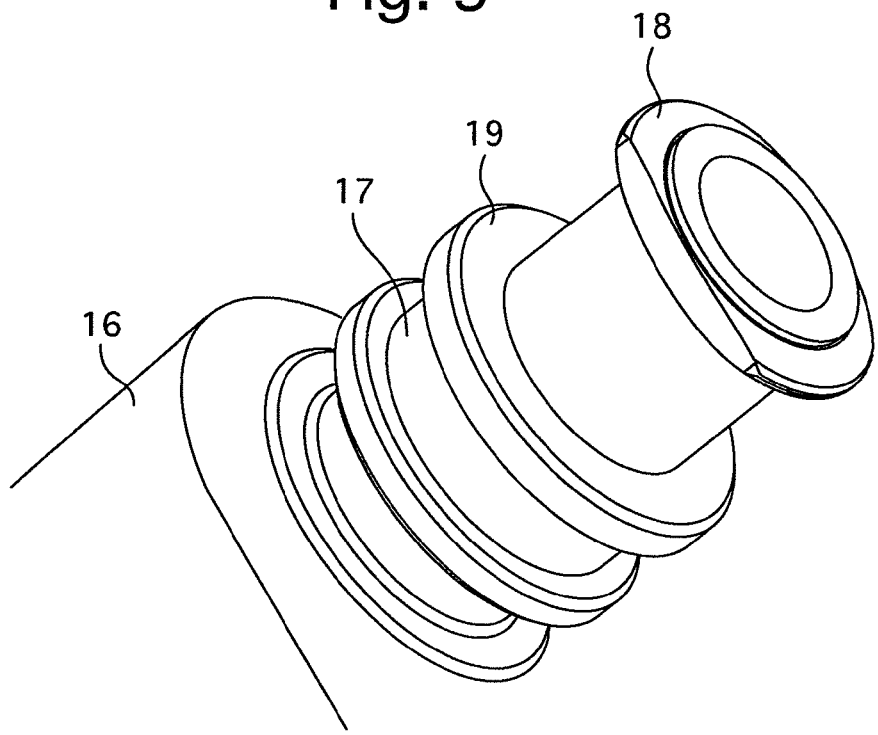
FIG. 3 is a perspective view of a pipe sleeve of the ultrasonic endoscope.
Figure 4:
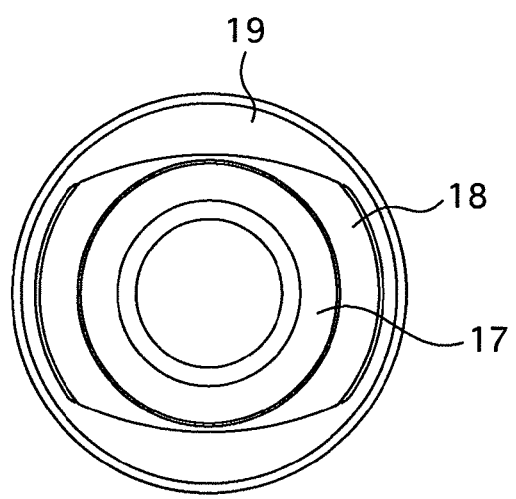
FIG. 4 is a front elevational view of the pipe sleeve.
Figure 5:
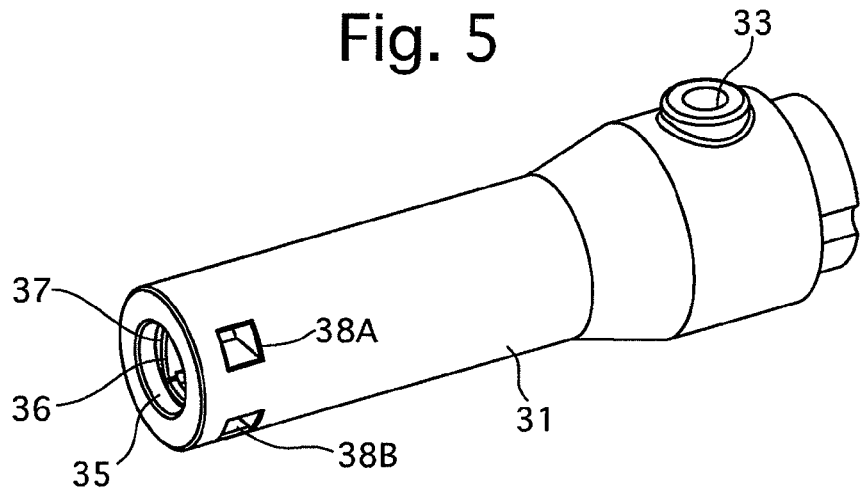
FIG. 5 is a perspective view of a cylindrical connecting body of the puncture needle device.
Figure 6:
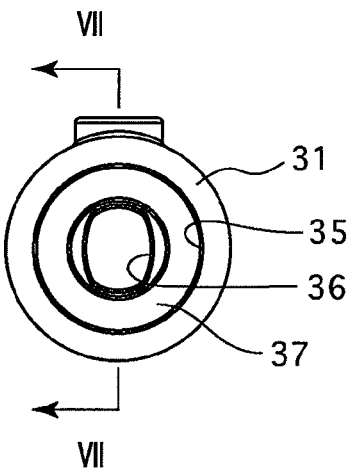
FIG. 6 is a front elevational view of the cylindrical connecting body.
Figure 7:
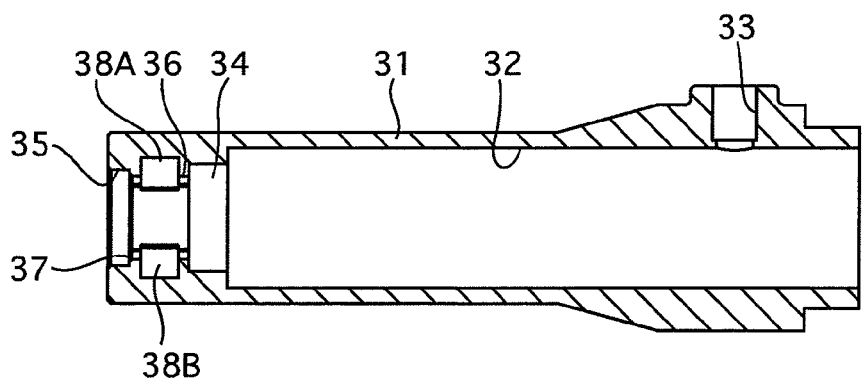
FIG. 7 is a cross sectional view taken along the line VII-VII shown in FIG. 6 and viewed in the direction of the appended arrows.

The ultrasonic endoscope 10 is provided with the control body 11, the insertion portion 13, a light guide tube (not shown) and an ultrasonic image transmission tube (not shown). The insertion portion 13 extends forward from the control body 11 and is provided at the front end with an ultrasonic probe 12. Both the light guide tube and the ultrasonic image transmission tube extend from the control body 11 in a direction opposite to the direction of extension of the insertion portion 13. The light guide tube is provided at a rear end thereof with a connector (light source connector) for connection to a light source (not shown), and the ultrasonic image transmission tube is provided at a rear end thereof with a connector (ultrasonic image connector) for connection to an ultrasonic diagnostic equipment (not shown). The insertion portion 13 is provided in the vicinity of the distal end (front end) thereof with a bending portion (bendable portion) 14 which bends in the upward/downward direction by operating a bending control lever 15 provided on the control body 11. The control body 11 is provided with a treatment tool insertion protrusion 16 which protrudes outwardly from a front part of the control body 11, and is further provided with a pipe sleeve 17 which projects obliquely rearwards from a rear end surface of the treatment tool insertion protrusion 16. The pipe sleeve 17 is in the shape of a substantially hollow cylinder, and both ends of the pipe sleeve 17 are formed as open ends. The pipe sleeve 17 is made of an austenitic stainless steel (more specifically, JIS (Japan Industrial Standard) SUS304). As shown in FIGS. 3, 4 and others, the pipe sleeve 17 is provided, on an outer peripheral surface thereof in the vicinity of the outer end of the pipe sleeve 17, with a non-circular-shaped collar 18 which is formed integral with the pipe sleeve 17 to project radially outwards from the pipe sleeve 17. The collar 18 is formed in such a manner so as to have cut-off opposite end portions of an imaginary circular collar along a pair of circular arcs (the lengths thereof are mutually identical) symmetrically positioned with respect to the center of the imaginary circular collar. In addition, the pipe sleeve 17 is provided, on an outer peripheral surface thereof at a position different from the position of the collar 18 in the axial direction of the pipe sleeve 17, with an annular flange (flange) 19 in the shape of a circular ring as viewed from the front. The outer diameter of the annular flange 19 is slightly greater than the longitudinal size (length) of the collar 18 (the diameter of the aforementioned imaginary circular collar), and the annular flange 19 (and the surface thereof which faces the collar 18) lies in a plane orthogonal to the axis of the pipe sleeve 17.

In addition, the control body 11 and the insertion portion 13 are provided therethrough with an internal conduit 20 (shown by a broken line in FIG. 1), the rear end of which is connected to the pipe sleeve 17. The front end of the internal conduit 20 is connected to a treatment tool opening 21 which is formed in the insertion portion 13 at a position immediately behind the ultrasonic probe 12.

The ultrasonic image connector of the ultrasonic image transmission tube is connected to the aforementioned ultrasonic diagnostic equipment (not shown), the ultrasonic diagnostic equipment is connected to a CRT monitor (not shown), and the ultrasonic probe 12 is covered with a rubber balloon (not shown). Thereafter, upon an ultrasonic image visualization switch of the ultrasonic diagnostic equipment being turned ON, an ultrasonic wave is sent out from the surface of the ultrasonic probe 12 toward an test object (not shown), and the ultrasonic wave reflected by a surface of the test object to be incident on the ultrasonic probe 12 is received by the ultrasonic probe 12. An ultrasonic wave signal transmission cable (not shown) via which the ultrasonic probe 12 and the ultrasonic image connector are connected is inserted into the insertion portion 13, the control body 11 and the ultrasonic image transmission tube so that the ultrasonic wave signal received by the ultrasonic probe 12 is electrically processed by the ultrasonic diagnostic equipment and displayed on the CRT monitor.

The structure of the puncture needle device 30 will be discussed hereinafter.

The puncture needle device 30 is provided with a cylindrical connecting body 31 which is in the shape of a substantially circular cylinder and made of a hard resin (e.g., PC (polycarbonate), Noryl, or the like, which are resin materials sterilizable by EOG). A slider support hole 32 is formed through the cylindrical connecting body 31 except a front internal portion thereof. A female screw hole 33, through which the slider support hole 32 and the outer space of the cylindrical connecting body 31 are communicatively connected to each other, is formed as a through-hole in a rear portion of the cylindrical connecting body 31 (see FIG. 7). The front end of the slider support hole 32 is communicatively connected with an intermediate circular hole 34 which is formed in the cylindrical connecting body 31 immediately in front of the front end of the slider support hole 32. The intermediate circular hole 34 is smaller in diameter than the slider support hole 32 and coaxial with the slider support hole 32. The cylindrical connecting body 31 is provided at the front end thereof with an anti-tilt recess 35 which is recessed to have the same cross sectional shape as the annular flange 19 of the pipe sleeve. A collar receiving hole 36 is formed in the cylindrical connecting body 31 between the intermediate circular hole 34 and the anti-tilt recess 35 and is coaxial with the intermediate circular hole 34 and the anti-tilt recess 35. The collar receiving hole 36 has the same front elevational shape as that of the collar 18 of the pipe sleeve 17, and is non-circular in shape and smaller in size than each of the intermediate circular hole 34 and the anti-tilt recess 35. The bottom surface (rear surface) in the anti-tilt recess 35 is formed as an insertion limit surface (insertion limit portion) 37 which lies in a plane orthogonal to the axis of the cylindrical connecting body 31. The cylindrical connecting body 31 is provided in a front portion thereof with a pair of support through-holes 38A and 38B that are parallel to each other and extend through the front portion in a direction orthogonal to the axis of the cylindrical connecting body 31.

The puncture needle device 30 is provided with a first slider 40 which is cylindrical in shape and made of a hard resin (e.g., PC (polycarbonate) or the like). The first slider 40 is inserted into the cylindrical connecting body 31 from the rear end opening thereof to be freely slidable. Both ends (front and rear ends) of the first slider 40 are open ends which are substantially identical in outer diameter to the diameter of the slider support hole 32. The puncture needle device 30 is provided at the rear end of the first slider 40 with a first stopper 41. The first stopper 41 is made of a hard resin, greater in diameter than the slider support hole 32 and fixed to the rear end of the first slider 40. Therefore, the first slider 40 is slidable between a fully-plunged position, at which the first stopper 41 comes in contact with the rear end surface of the cylindrical connecting body 31, and a fully-withdrawn position, at which the first slider 40 is prevented from being further withdrawn rearward by a stopper (not shown). In addition, a first fixing screw 43 is inserted (screwed) into the female screw hole 33, and the position of the first slider 40 relative to the cylindrical connecting body 31 can be fixed by the end surface (inner end surface) of the shaft (threaded shaft) of the first fixing screw being pressed against (screwed against) an outer peripheral surface of the first slider 40. The puncture needle device 30 is provided with a flexible sheath 44, both ends of which are open, which is made of a flexible material such as resin. The sheath 44 is fixed at the rear end thereof to an inner surface of the first stopper 41 to be concentric with the first slider 40. The front of the sheath 44 passes through the slider support hole 32, the intermediate circular hole 34, the collar receiving hole 36 and the anti-tilt recess 35 to project outwardly therefrom, toward the front of the cylindrical connecting body 31. Accordingly, the amount of projection of the sheath 44 from the cylindrical connecting body 31 can be adjusted by changing the slide position of the first slider 40 and the first stopper 41 relative to the cylindrical connecting body 31.

The puncture needle device 30 is provided with a second slider 45, which is cylindrical in shape and made of a hard resin (e.g., PC (polycarbonate) or the like), is inserted into the first slider 40 from the rear end opening thereof to be freely slidable therein. The outer diameter of the second slider 45 is smaller than the inner diameter of the first slider 40. Both ends (front and rear ends) of the second slider 45 are open ends, and a rear end fixed member 46 made of a hard resin (e.g., PC (polycarbonate), Noryl or the like) is fixed to the rear end of the second slider 45. The rear end fixed member 46 is formed so that a rear part is smaller in diameter than a front part, and is provided on an outer peripheral surface of the rear part with a male thread. In addition, the puncture needle device 30 is provided around an outer peripheral surface of the second slider 45 with a second stopper 48. The second stopper 48 is made of a hard resin (e.g., PC (polycarbonate) or the like) and fitted on the second slider 45 to be freely slidable thereon. The second stopper 48 is provided with a female through-hole (not shown) which extends in a radial direction of the second stopper 48, and a second fixing screw 49 similar to the first fixing screw 43 is inserted (screwed) into this female screw hole. Accordingly, the slide position of the second stopper 48 relative to the second slider 45 can be fixed by the end surface (inner end surface) of the shaft (threaded shaft) of the second fixing screw being pressed against (screwed against) an outer peripheral surface of the second slider 45. The second slider 45 and the rear end fixed member 46 are slidable relative to the first slider 40 and the first stopper 41 between a plunged position, at which the second stopper 48 comes in contact with the rear end surface of the first stopper 41, and a fully-withdrawn position, in which the second slider 45 is prevented from being further withdrawn rearward with respect to the first slider 40 and the first stopper 41 by a stopper (not shown). In addition, the plunged position of the second slider 45 and the rear end fixed member 46 can be adjusted by adjusting the slide position of the second stopper 48 relative to the second slider 45. The puncture needle device 30 is provided with a puncture needle (centesis needle) 51 made of resilient metal and is formed as a hollow member, and the rear open end of the puncture needle 51 is fixed to an inner surface of the rear end fixed member 46 to be concentric therewith. The front (tip) of the puncture needle 51 passes through the inside of the sheath 44 to project outwardly therefrom, toward the front, and the puncture needle 51 is provided in the vicinity of the front end thereof with an opening 52. Accordingly, the amount of projection of the front end of the puncture needle 51 from the sheath 44 can be adjusted by changing the slide position of the second slider 45 (the rear end fixed member 46) relative to the first slider 40.

In addition, the female screw thread formed on an inner peripheral surface of the stylet support cap 55, that is cylindrical in shape and made of a hard resin (e.g., POM or the like), is disengageably screw-engaged with the aforementioned male thread that is formed in the rear of the rear end fixed member 46. The rear end of a stylet 56 (see FIGS. 10 and 11) made as a resilient member is fixed to the stylet support cap 55. The stylet 56 is inserted into the internal space of the puncture needle 51 from the rear end opening thereof to be relatively movable therein.

The puncture needle device 30 is provided with a lock member 60 mounted to the front of the cylindrical connecting body 31 through the pair of support through-holes 38A and 38B.

The lock member 60 is generally a rod-like member consisting of a pair of slide members 61 and two control knobs 66 and 68. The pair of slide members 61 pass (extend) through the pair of support through-holes 38A and 38B, respectively, and are made of metal such as brass or SUS (stainless used steel). The two control knobs 66 and 68 are each made of a hard resin such as PC (polycarbonate). The common ends on one side of the pair of slide members 61 are connected to each other by the control knob 66 and the common ends on the other side of the pair of slide members 61 are connected to each other by the control knob 68.

Figure 8:
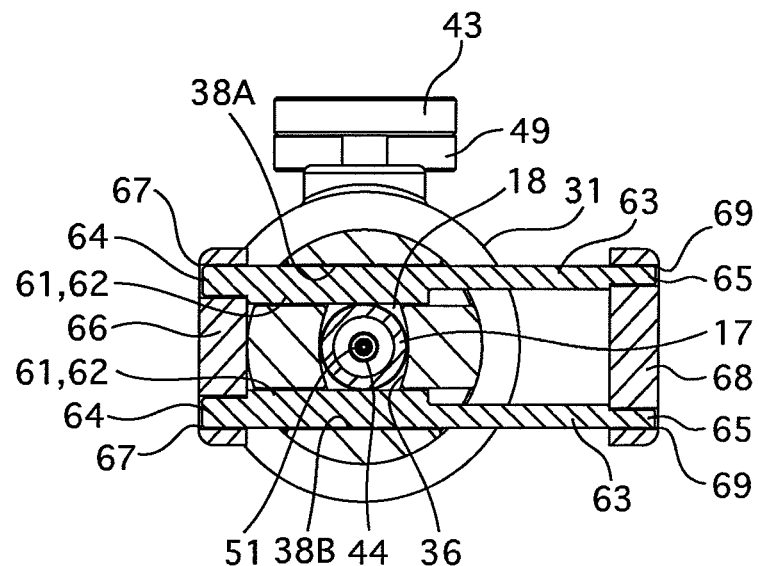
FIG. 8 is a cross sectional view taken along the line VIII-VIII shown in FIG. 1 and viewed in the direction of the appended arrows in a state where a lock member of the puncture needle device is in the locked position preventing the puncture needle device from being detached from the ultrasonic endoscope.
Figure 9:
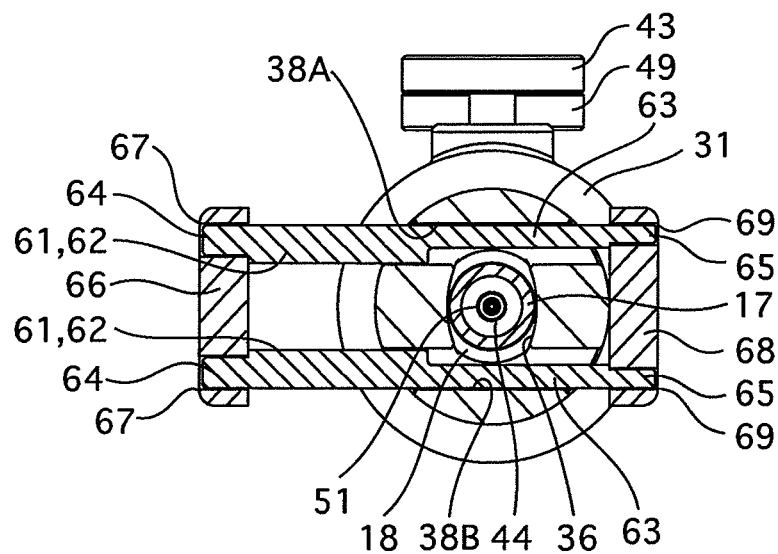
FIG. 9 is a view similar to that of FIG. 8 in a state where the lock member of the puncture needle device is in an unlocked position allowing the puncture needle device to be attached and detached to and from the ultrasonic endoscope.

As shown in FIGS. 8 and 9, each slide member 61 of the lock member 60 is provided with a stopper portion 62 and a passage allowing portion 63 that is smaller (narrower) in cross section than the stopper portion 62. The stopper portion 62 of one slide member 61 (the upper slide member 61 with respect to FIGS. 8 and 9) has substantially the same cross-sectional shape as that of the through-hole 38A and the stopper portion 62 of the other slide member 61 (the lower slide member 61 with respect to FIGS. 8 and 9) has substantially the same cross-sectional shape as that of the through-hole 38B. The passage allowing portion 63 of one slide member 61 (the upper slide member 61 with respect to FIGS. 8 and 9) has a smaller cross-sectional size than the through-hole 38A, and the passage allowing portion 63 of the other slide member 61 (the lower slide member 61 with respect to FIGS. 8 and 9) has a smaller cross-sectional size than the through-hole 38B. Each slide member 61 is provided at an outer end of the stopper portion 62 with an engaging projection 64 smaller in width than the stopper portion 62 and is provided at an outer end of the passage allowing portion 63 with an engaging projection 65 smaller in width than the passage allowing portion 63. The control knob 66 is provided with a pair of mounting holes 67 in which the engaging projections 64 of the pair of slide members 61 are disengageably engaged, respectively, and the control knob 68 is provided with a pair of mounting holes 69 in which the engaging projections 65 of the pair of slide members 61 are disengageably engaged, respectively.

When the lock member 60 is mounted (assembled) onto the cylindrical connecting body 31, the passage allowing portions 63 and the engaging projections 65 of the pair of slide members 61 are inserted into the pair of support through-holes 38A and 38B, respectively, with the engaging projections 64 of the pair of slide members 61 being engaged in the mounting holes 67 of the control knob 66, respectively. Subsequently, the engaging projections 65 of the pair of slide members 61 are fitted into the pair of mounting holes 69 of the control knob 68 after being made to project outward from the pair of support through-holes 38A and 38B, respectively. Therefore, since the lock member 60 is composed of the pair of slide members 61 and the two control knobs 66 and thus having simple structure, the number of elements of the lock member 60 is small and the lock member 60 can be mounted to the cylindrical connecting body 31 in an easy manner. Moreover, the lock member 60 can be easily disassembled in the reverse procedure to the above-described procedure of assembling the lock member 60.

The mounting/dismounting procedure (assembling/disassembling procedure) of the puncture needle device 30 to and from the pipe sleeve 17 and the operating procedure of the puncture needle device 30 will be discussed hereinafter.

Figure 10:
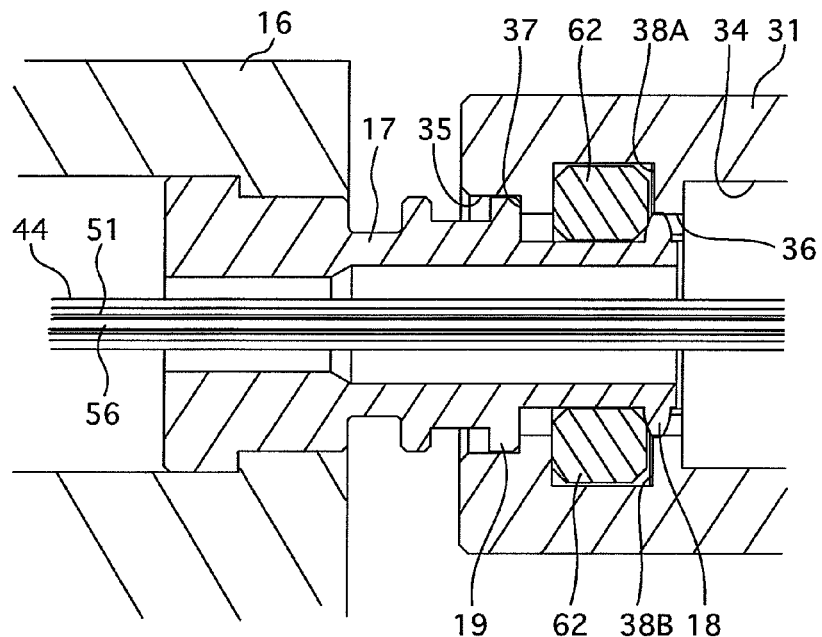
FIG. 10 is a cross sectional view taken along the line X-X shown in FIG. 1 and viewed in the direction of the appended arrows in a state where the lock member is in the locked position.
Figure 11:
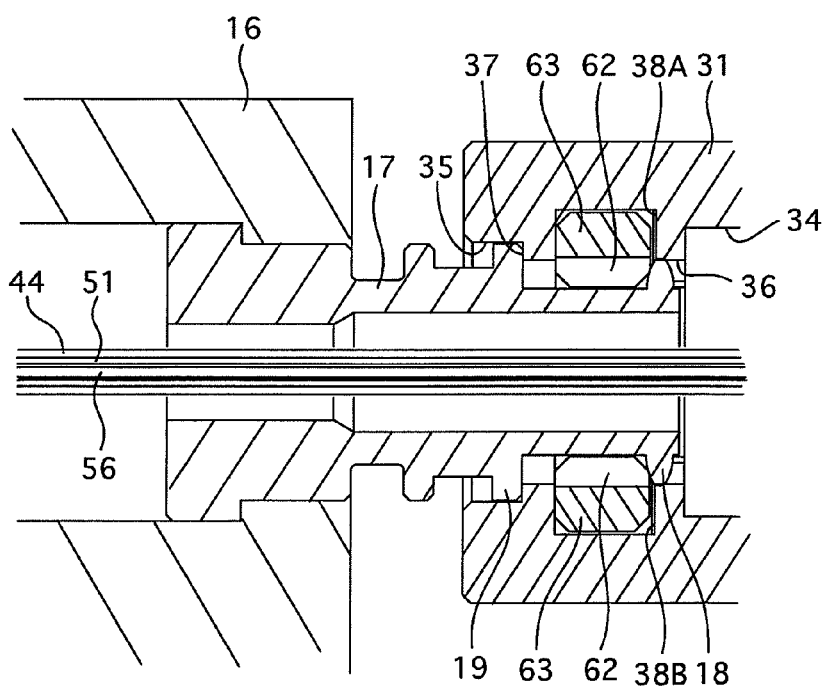
FIG. 11 is a view similar to that of FIG. 10 in a state where the lock member is in the unlocked position.

When the puncture needle device 30 (separated from the ultrasonic endoscope 10) is mounted onto the pipe sleeve 17, firstly the lock member 60 is moved to the unlocked position shown in FIGS. 9 and 11 by pressing the control knob 68 toward the control knob 66 side with respect to the cylindrical connecting body 31. Subsequently, after the cylindrical connecting body 31 is positioned coaxially with the pipe sleeve 17 while the orientation of the collar receiving hole 36 of the cylindrical connecting body 31 is made to correspond to the orientation of the pipe sleeve 17 and the collar 18, the anti-tilt recess 35 of the cylindrical connecting body 31 is brought close to the pipe sleeve 17 to engage onto the collar 18 of the pipe sleeve 17. As shown in FIG. 9, the distance between the passage allowing portions 63 of the pair of slide members 61 is greater than the dimensions of the collar receiving hole 36 and the collar 18 in the same direction (the vertical direction with respect to FIG. 9). Accordingly, inserting the pipe sleeve 17 into the cylindrical connecting body 31 to a predetermined position therein by further bringing the cylindrical connecting body 31 close to the pipe sleeve 17 side causes the collar 18 to be engaged in the collar receiving hole 36 through the space between the passage allowing portions 63 of the pair of slide members 61, and causes a peripheral surface of the annular flange 19 of the pipe sleeve 17 to come in surface contact with a ring-shaped inner peripheral surface in the anti-tilt recess 35, and also causes a surface of the annular flange 19 on the collar 18 side to come in surface contact with the insertion limit surface 37 (see FIGS. 9 and 11). In this state, moving the lock member 60 to the locked position shown in FIG. 8 by pushing the control knob 66 into the cylindrical connecting body 31 toward the other control knob 68 causes each of the stopper portions 62 of the pair of slide members 61 to come in contact with a surface of the collar 18 on the annular flange 19 side (see FIGS. 8 and 10).

Once the lock member 60 is positioned as shown in FIGS. 8 and 10, the cylindrical connecting body 31 is prevented from moving in a dismounting direction relative to the pipe sleeve 17 (i.e., from moving in a direction toward the stylet support cap 55) by engagement of the stopper portions 62 of the pair of the pair of slide members 61 with the collar 18, and is prevented from further moving in an inserting direction relative to the pipe sleeve 17 (i.e., from moving in a direction toward the distal ends of the sheath 44 and the puncture needle 51) by engagement of the annular flange 19 with the insertion limit surface 37. Accordingly, the cylindrical connecting body 31 is totally prevented from moving relative to the pipe sleeve 17 in the axial direction thereof. Moreover, the cylindrical connecting body 31 is totally prevented from rotating relative to the pipe sleeve 17 about the axis thereof since the collar 18 and the collar receiving hole 36, which are mutually identical in shape and both non-circular in shape, are engaged with each other. Furthermore, since the annular flange 19, which is formed on the pipe sleeve 17 at a position different from the position of the collar 18 in the axial direction of the pipe sleeve 17, is brought into surface contact with the insertion limit surface 37 while a peripheral surface of the annular flange 19 is made in surface contact with an inner peripheral surface in the anti-tilt recess 35, the cylindrical connecting body 31 is also totally prevented from tilting relative to the pipe sleeve 17.

In this manner, the puncture needle device 30 is fully prevented from moving relative to the pipe sleeve 17 (the ultrasonic endoscope 10), and the operator can manipulate the puncture needle device 30 connected to the ultrasonic endoscope 10 with precision while viewing the image displayed on the CRT monitor. Namely, the operator can precisely manipulate the sheath 44, the puncture needle 51 and the stylet 56 by sliding the first stopper 41 and the rear end fixed member 46 or moving the stylet 56 forward and rearward relative to the puncture needle 51 with the screw engagement of the stylet support cap 55 with the rear end fixed member 46 being released.

When an endoscopic operation using the puncture needle device 30 is completed or when it is desired to insert a treatment tool different from the puncture needle device 30 into the pipe sleeve 17, the operator (user) moves the lock member 60 to the unlocked position shown in FIGS. 9 and 11 by pushing the control knob 68 toward the control knob 66 side with respect to the cylindrical connecting body 31. This movement of the lock member 60 to the unlocked position causes the stopper portions 62 of the pair of slide members 61 to move sideways from a surface of the collar 18 on the annular flange 19 side, thereby allowing the collar 18 of the pipe sleeve 17 to pass through the space between the passage allowing portions 63 of the pair of slide members 61. Therefore, if the operator moves the cylindrical connecting body 31 toward the stylet support cap 55 side (i.e., in a direction away from the pipe sleeve 17) along the axis of the cylindrical connecting body 31, the collar 18 of the pipe sleeve 17 moves out of the collar receiving hole 36, which completes the dismounting operation for the cylindrical connecting body 31 from the pipe sleeve 17 of the control body 11.

A second embodiment of the puncture needle device for ultrasonic endoscope according to the present invention will be hereinafter discussed with reference to FIGS. 12 through 16. Elements and components of the second embodiment of the puncture needle device which are similar to those of the first embodiment of the puncture needle device are designated by the same reference numerals, and detailed descriptions of such elements and components are omitted.

The structure of a puncture needle device 70 according to the second embodiment will be discussed hereinafter.

The puncture needle device 70 is provided with a cylindrical connecting body 71 which is in the shape of a substantially circular cylinder and made of the same material as the cylindrical connecting body 31. A slider support hole 32 is formed through the cylindrical connecting body 71 except a front internal portion thereof, and a female screw hole 33 (not shown in FIGS. 12 through 16), through which the slider support hole 32 and the outer space of the cylindrical connecting body 71 are communicatively connected to each other, is formed as a through-hole in a rear portion of the cylindrical connecting body 71. The cylindrical connecting body 71 is provided at the front end thereof with an annular recess 72 which is recessed rearward and shaped into a ring as viewed from the front. A female thread 73 is formed on the inner peripheral surface of the annular recess 72. A collar receiving hole 36 is formed in the cylindrical connecting body 71 between the slider support hole 32 and the annular recess 72 to be coaxial with the slider support hole 32 and the annular recess 72. The front end of slider support hole 32 and the rear end of the annular recess 72 are communicatively connected to each other via the collar receiving hole 36. The collar receiving hole 36 is smaller in cross-sectional shape than slider support hole 32 and the annular recess 72.

An elastic washer (elastic insertion limit portion) 75 is seated on the bottom surface (rear end surface) of the annular recess 72. The elastic washer 75 is a ring member smaller in diameter than the annular recess 72 and made of an elastic material such as silicon rubber. In addition, a male thread 77 formed on a male-threaded bushing 76 made of a hard resin (e.g., PC (polycarbonate), Noryl or the like) is screw-engaged with the female thread 73, and the elastic washer 75 is positioned between the base surface of the annular recess 72 and the male-threaded bushing 76. The inner diameter of the elastic washer 75 in a free state is slightly smaller than the outer diameter of the annular flange 19 and is greater (or can be smaller) than the diameter of the imaginary circular collar that defines the collar 18 (longitudinal size). In addition, a rear part (annular surface) 78 of the inner hole (inner peripheral surface) of the male-threaded bushing 76 has the same shape and size as a peripheral surface of the annular flange 19, while a front part of the inner hole of the male-threaded bushing 76 is tapered.

The cylindrical connecting body 71 is provided in a front portion thereof with a pair of support through-holes 38A and 38B that are parallel to each other, and a lock member 60 is slidably mounted to the front portion of the cylindrical connecting body 71 through the pair of support through-holes 38A and 38B.

Figure 12:
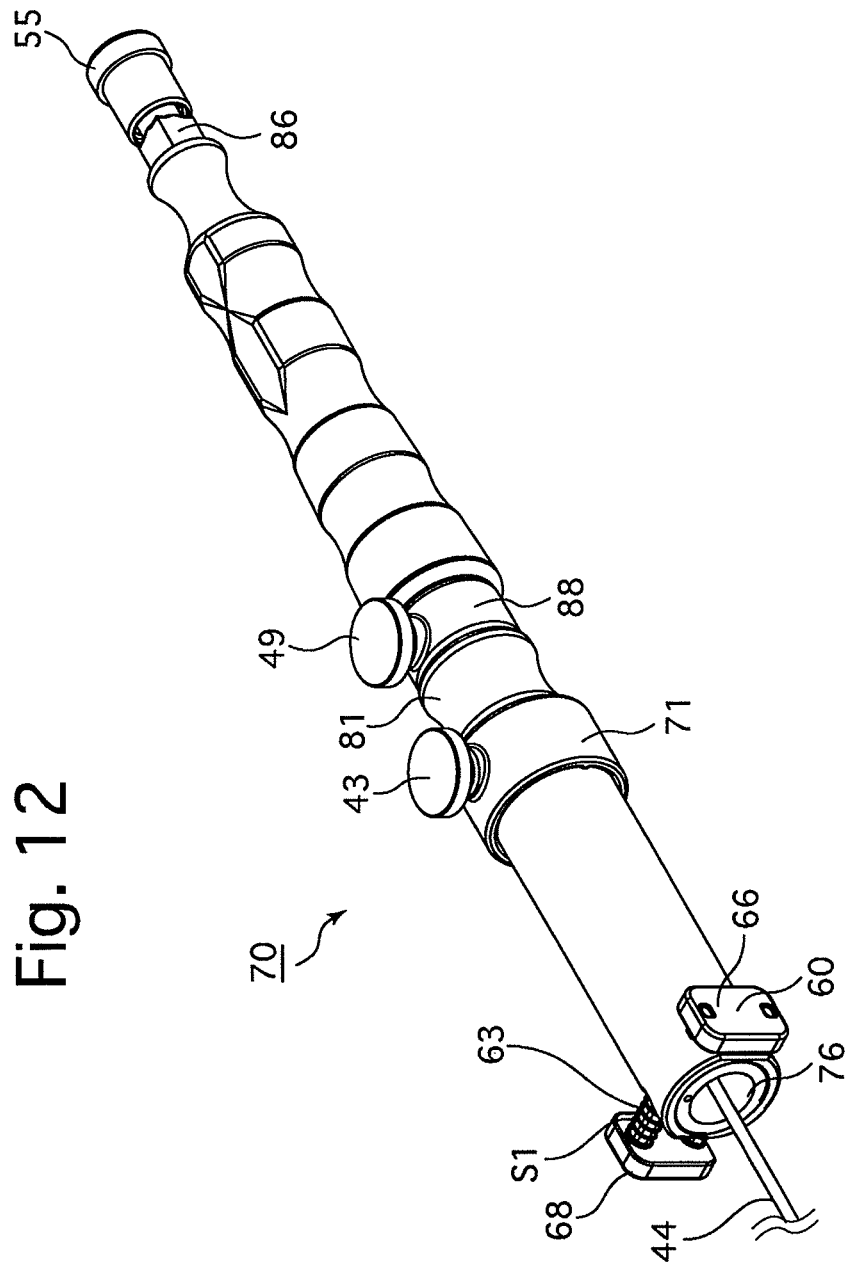
FIG. 12 is a perspective view of a second embodiment of the puncture needle device in a state where the control portion thereof is in the fully-contracted state.
Figure 13:
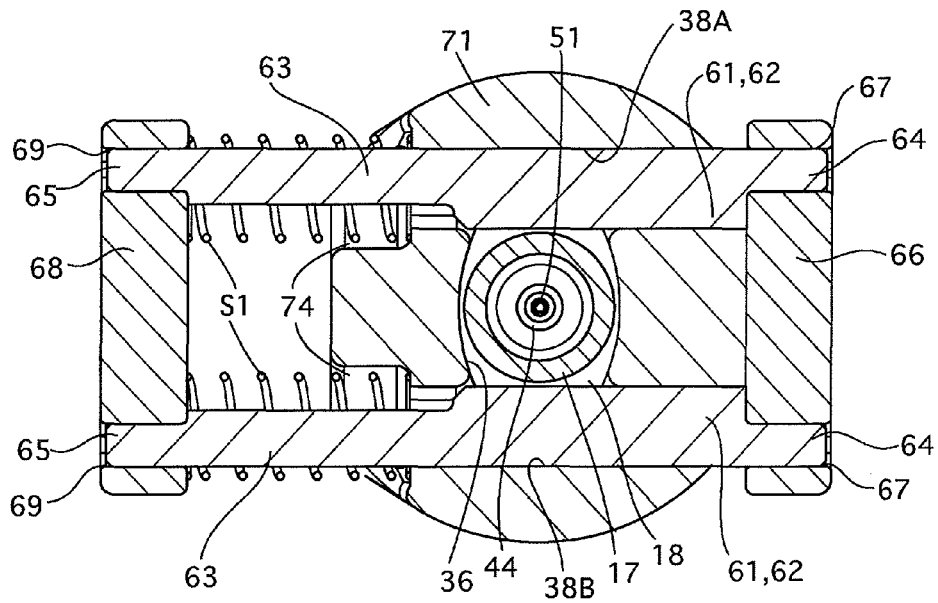
FIG. 13 is a view similar to that of FIG. 8, showing a state where the lock member of the puncture needle device shown in FIG. 12 is in the locked position.
Figure 14:
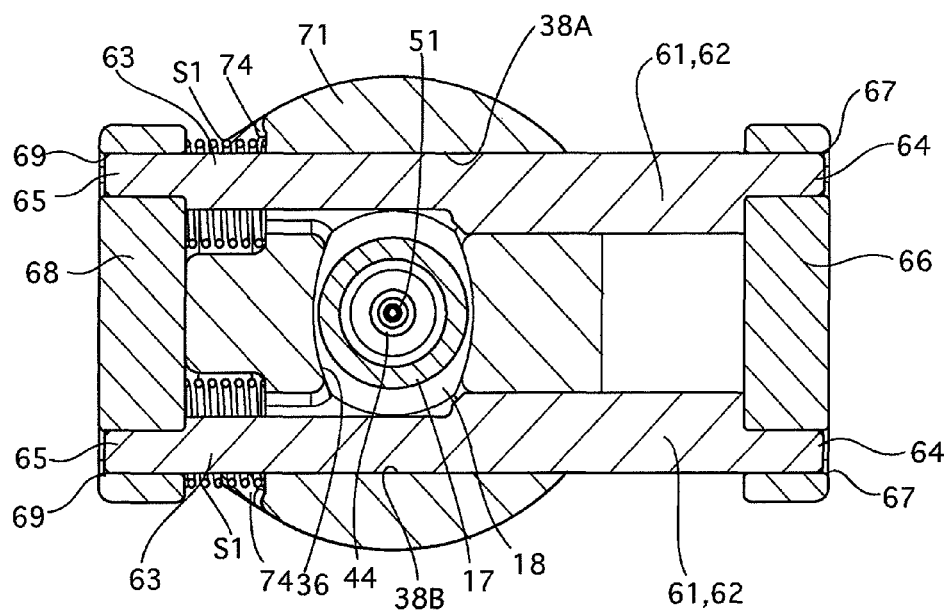
FIG. 14 is a view similar to that of FIG. 9, showing a state where the lock member of the puncture needle device shown in FIG. 12 is in the unlocked position.

As shown in FIGS. 12 through 14, the cylindrical connecting body 71 is provided, on a portion of the outer peripheral surface thereof which faces the control knob 68, with a pair of support recesses 74 which are communicatively connected to the end openings (left end openings with respect to FIGS. 13 and 14) of the pair of support through-holes 38A and 38B on the control knob 68 side, respectively. A pair of compression coil springs (biaser) S1 are placed over the passage allowing portions 63 of the pair of slide members 61, respectively, and the opposite ends of each compression coil spring S1 are in contact with the base of the associated support recess 74 and the control knob 68, respectively. The pair of compression coil springs S1 are continuously compressed (resiliently deformed) regardless of whether the lock member 60 is in the locked position, the unlocked position, or any position therebetween. Accordingly, upon the operator releasing his/her hand from the lock member 60, the lock member 60 moves to the locked position shown in FIGS. 13 and 15 and is held thereat by the biasing force of the pair of compression coil springs S1. Thereafter, if the control knob 68 is pushed toward the pair of support through-holes 38A and 38B against the biasing force of the pair of compression coil springs S1, the lock member 60 moves to the unlocked position shown in FIGS. 14 and 16.

The puncture needle device 70 is provided with a first slider 40 (not shown in FIGS. 12 through 16) which is inserted into the cylindrical connecting body 71 from the rear end opening thereof to be freely slidable. The puncture needle device 70 is provided at the rear end of the first slider 40 with a first stopper 81. The first stopper 81 is made of a hard resin, greater in diameter than the slider support hole 32 and fixed to the rear end of the first slider 40. A sheath 44 is fixed at the rear end thereof to the frontend of the first slider 40. The puncture needle device 70 is provided with a second slider 45 (not shown in FIGS. 12 through 16) which is inserted into the first slider 40 to be freely slidable, and a rear end fixed member 86 made of a hard resin (e.g., PC (polycarbonate), Noryl or the like) is fixed to the rear end of the second slider 45. In addition, the puncture needle device 70 is provided on an outer peripheral surface of the second slider 45 with a second stopper 88 which is made of a hard resin (e.g., PC (polycarbonate) or the like) and fitted on the second slider 45 to be freely slidable thereon. The second stopper 88 is provided with a female through-hole (not shown) which extends in a radial direction of the second stopper 88, and a second fixing screw 49 is inserted (screwed) into this female screw hole. Additionally, the female screw thread formed on an inner peripheral surface of the stylet support cap that supports the rear end of the stylet 56 is disengageably screw-engaged with the male thread formed in the rear of the rear end fixed member 86.

The first stopper 81, the rear end fixed member 86 and the second stopper 88 in the second embodiment of the puncture needle device 70 have the same basic structure (although different in specific shape) as those of the first stopper 41, the rear end fixed member 46 and the second stopper 48 in the first embodiment of the puncture needle device 30. Furthermore, the first stopper 81, the rear end fixed member 86 and the second stopper 88 in the second embodiment of the puncture needle device 70 are mounted to peripheral parts thereof in the same manner as that of the first stopper 41, the rear end fixed member 46 and the second stopper 48 in the first embodiment of the puncture needle device 30. Accordingly, basic operations (the expansion/contraction (plunging) operation of the entire puncture needle device 70, slide operations of the sheath 44, the puncture needle 51 and the stylet 56, etc.) of the puncture needle device 70 are the same as those of the puncture needle device 30.

The mounting/dismounting procedure of the puncture needle device 70 to and from the pipe sleeve 17 will be discussed hereinafter.

Figure 16:
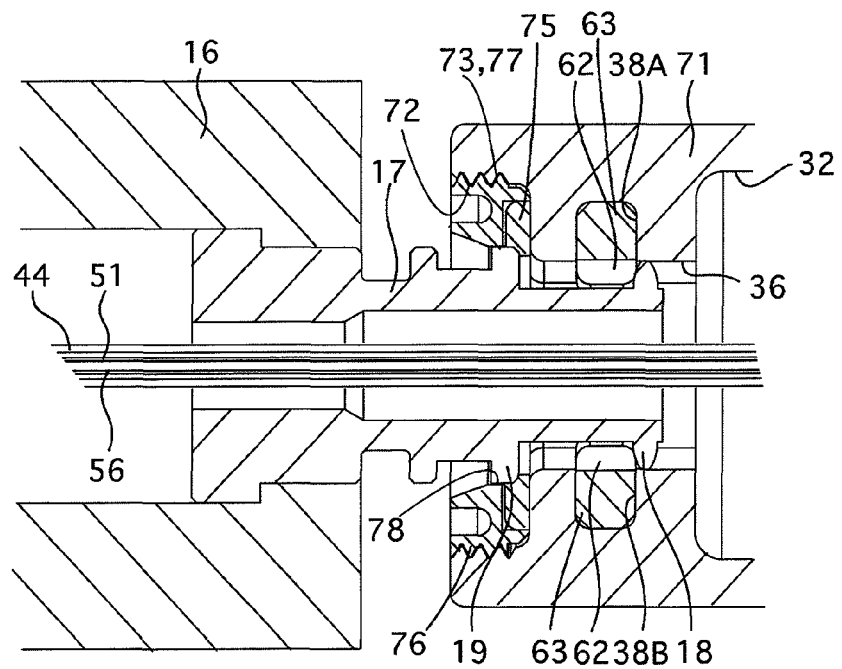
FIG. 16 is a view similar to that of FIG. 11, showing a state where the lock member is in the unlocked position.

When the puncture needle device 70 separated from the ultrasonic endoscope 10 is mounted to the pipe sleeve 17, firstly the lock member 60 held in the locked position by the biasing force of the pair of compression coil springs S1 is moved to the unlocked position shown in FIGS. 14 and 16 against the biasing force of the pair of compression coil springs S1, and is held manually at this position by pressing the control knob 68 toward the control knob 66 side with respect to the cylindrical connecting body 71.

Subsequently, after the cylindrical connecting body 71 is positioned coaxially with the pipe sleeve 17 while the orientation of the collar receiving hole 36 of the cylindrical connecting body 71 is made to correspond to the orientation of the collar 18 of the pipe sleeve 17, the pipe sleeve 17 is inserted into the cylindrical connecting body 71 to a predetermined position therein. This insertion of the pipe sleeve 17 into the cylindrical connecting body 71 to this predetermined position causes the collar 18 to be engaged in the collar receiving hole 36 of the cylindrical connecting body 71 through the space between the passage allowing portions 63 of the pair of slide members 61, and causes the annular flange 19 of the pipe sleeve 17 to come in press contact with a front surface of the elastic washer 75 (which is positioned more radially inward than the male-threaded bushing 76) to thereby elastically deform (depress) this contacting portion of the elastic washer 75 rearward, and further causes a peripheral surface of the annular flange 19 to come in surface contact with the rear part 78 (annular surface) of the inner peripheral surface (inner hole) of the male-threaded bushing 76 (see FIGS. 14 and 15).

Figure 15:
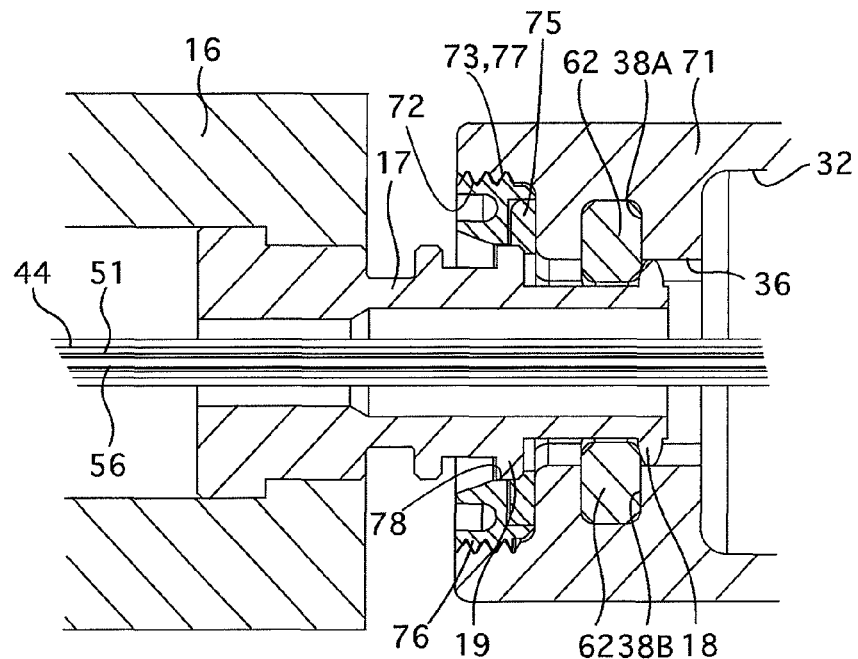
FIG. 15 is a view similar to that of FIG. 10, showing a state where the lock member is in the locked position.

In this state, upon the operator (user) releasing his/her hand from the lock member 60, the lock member 60 automatically slides to the locked position by the biasing force of the pair of compression coil springs S1 to thereby bring each of the stopper portions 62 of the pair of slide members 61 into surface contact with a surface of the collar 18 on the annular flange 19 side (see FIGS. 13 and 15).

Once the lock member 60 is positioned as shown in FIGS. 13 and 15, the cylindrical connecting body 71 is prevented from moving in a dismounting direction relative to the pipe sleeve 17 by engagement of the stopper portions 62 of the pair of the pair of slide members 61 with the collar 18, and is also prevented from moving in an inserting direction relative to the pipe sleeve 17 by engagement of the annular flange 19 with the elastic washer 75. Accordingly, the cylindrical connecting body 71 is totally prevented from rotating relative to the pipe sleeve 17 in the axial direction thereof.

In addition, the cylindrical connecting body 71 is prevented from rotating relative to the pipe sleeve 17 about the axis thereof by engagement of the collar 18 with the collar receiving hole 36, which are mutually identical in shape and both non-circular in shape.

Furthermore, since the annular flange 19, which is formed on the pipe sleeve 17 at a position different from the position of the collar 18 in the axial direction of the pipe sleeve 17, is in contact with the elastic washer 75 while a peripheral surface of the annular flange 19 is in surface contact with the rear part 78 of the inner peripheral surface of the male-threaded bushing 76, the cylindrical connecting body 71 is also totally prevented from tilting relative to the pipe sleeve 17.

When it is desired to dismount the puncture needle device 70 from the pipe sleeve 17, the operator moves the lock member 60 to the unlocked position against the biasing force of the pair of compression coil springs S1, and thereupon moves the puncture needle device 70 toward the stylet support cap 55 side (i.e., in a direction away from the pipe sleeve 17) along the axis of the puncture needle device 70 while holding the lock member 60 in the unlocked position to thereby remove the collar 18 and the annular flange 19 of the pipe sleeve 17 from the inside of the cylindrical connecting body 71.

As described above, in the third embodiment of the puncture needle device also, the puncture needle device 70 can be made immovable relative to the pipe sleeve 17.

In addition, upon the operator (user) releasing his/her hand from the lock member 60 after mounting the puncture needle device 70 to the pipe sleeve 17, the lock member 60 automatically slides to the locked position, which yields an improvement in connection operability of the puncture needle device 70 with the pipe sleeve 17. In addition, the puncture needle device 70 can be prevented from coming off the pipe sleeve 17 when the operator forgets to move the lock member 60 to the locked position.

Moreover, even in the case where an external force urging the lock member 60 to move toward the unlocked position is unexpectedly applied to the lock member 60, the lock member 60 is held in the locked position by the pair of compression coil springs S1, so that the locked state of the puncture needle device 70 by the lock member 60 is effectively prevented from being unexpectedly released.

Furthermore, since the elastic washer 75 comes in contact with the annular flange 19 while being elastically deformed when the puncture needle device 70 is connected to the pipe sleeve 17, no clearance is created between the annular flange 19 and the elastic washer 75, so that the cylindrical connecting body 71 can be prevented from rattling relative to the pipe sleeve 17 in an efficient manner.

If the puncture needle device 70 is made to slide toward the pipe sleeve 17 with a great force after the lock member 60 is moved to the locked position with the puncture needle device 70 connected to the pipe sleeve 17, the elastic washer 75 is greatly compressed, which may create a slight gap between the collar 18 and the stopper portions 62 of the pair of slide members 61. If such a gap is created, the frictional resistance produced between the collar 18 and the stopper portions 62 of the pair of slide members 61 disappears. Therefore, if the puncture needle device 70 were not equipped with the pair of compression coil springs S1, the lock member 60 would otherwise move by its own weight to the unlocked position, so that there is a possibility of the puncture needle device 70 coming off the pipe sleeve 17. However, this sort of problem hardly occurs in a structure like the puncture needle device 70 which holds the lock member 60 in the locked position using the pair of compression coil springs S1 that generates a biasing force capable of acting against the weight of the lock member 60.

A third embodiment of a puncture needle device for an ultrasonic endoscope according to the present invention will be hereinafter discussed with reference to FIGS. 17 and 18. Elements and components of the third embodiment of the puncture needle device which are similar to those of the first embodiment of the puncture needle device are designated by the same reference numerals, and detailed descriptions of such elements and components are omitted.

Although the puncture needle device 90 is provided with a cylindrical connecting body 91 having the same basic structure as the cylindrical connecting body 31, the cylindrical connecting body 91 is provided with a collar receiving hole 92 instead of the collar receiving hole 36 of the cylindrical connecting body 31. The collar receiving hole 92 is substantially rectangular as viewed from the front as shown in FIGS. 17 and 18. The collar receiving hole 92 is greater in size than the collar 18 of the pipe sleeve 17, and a clearance allowing relative rotation between the collar 18 and the collar receiving hole 92 (about the axis of the cylindrical connecting body 91) is created therebetween when the collar 18 is positioned in the collar receiving hole 92. However, the range of relative rotation between the collar 18 and the collar receiving hole 92 is limited to a range between a position shown in FIG. 18 at which inclined contact surfaces 18a and 18c of the collar 18 come in contact with the diagonally-positioned inner peripheral surface of the collar receiving hole 92 and another (opposite) position (not shown) at which inclined contact surfaces 18b and 18d of the collar 18 come in contact with the diagonally-positioned inner peripheral surface of the collar receiving hole 92.

Figure 17:
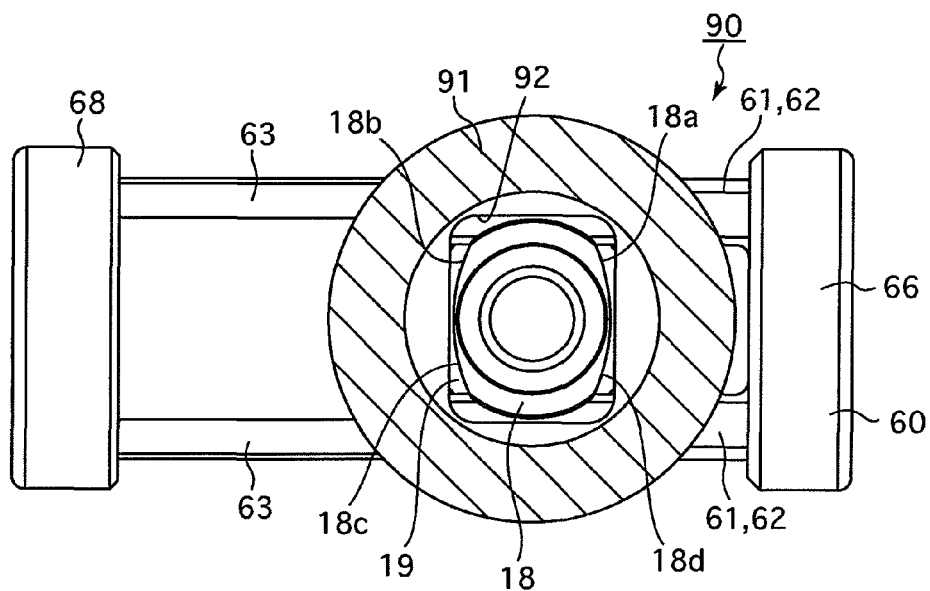
FIG. 17 is a view similar to that of FIG. 13, showing a state where the lock member of a third embodiment of the puncture needle device is in the locked position, taken along the line VIII-VIII shown in FIG. 1 and viewed in the direction opposite to the direction of the appended arrows.
Figure 18:
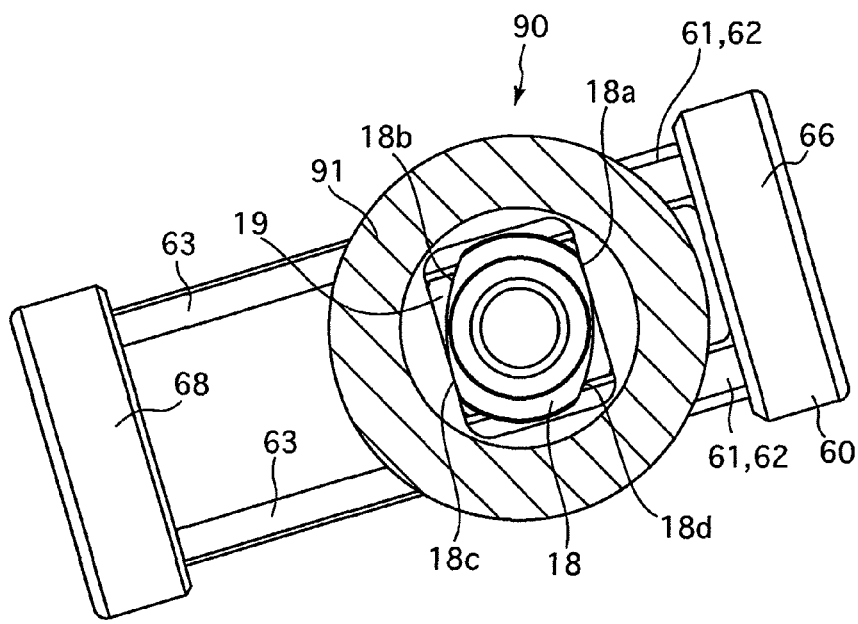
FIG. 18 is a view corresponding to that of FIG. 17, showing a state where the third embodiment of the puncture needle device has rotated relative to the pipe sleeve with the lock member of the puncture needle device remaining in the locked position.
Figure 19:
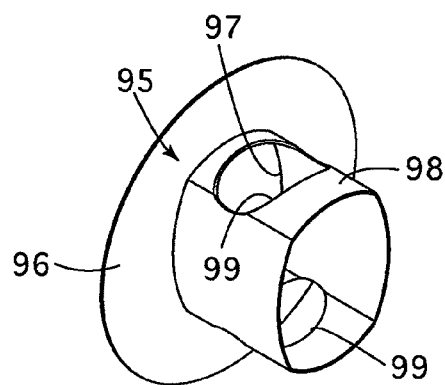
FIG. 19 is a perspective view of a reinforcing member provided as an element of a first modified embodiment of the puncture needle device.
Figure 20:
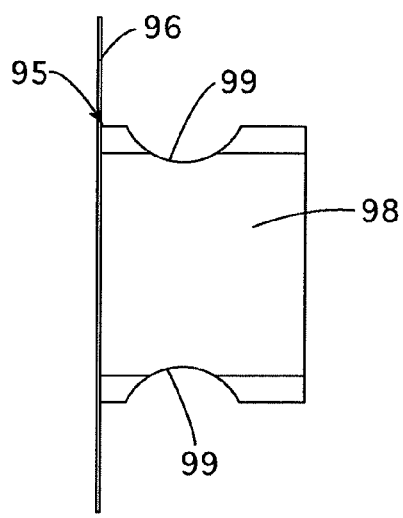
FIG. 20 is a side elevational view of the reinforcing member shown in FIG. 19.
Figure 21:
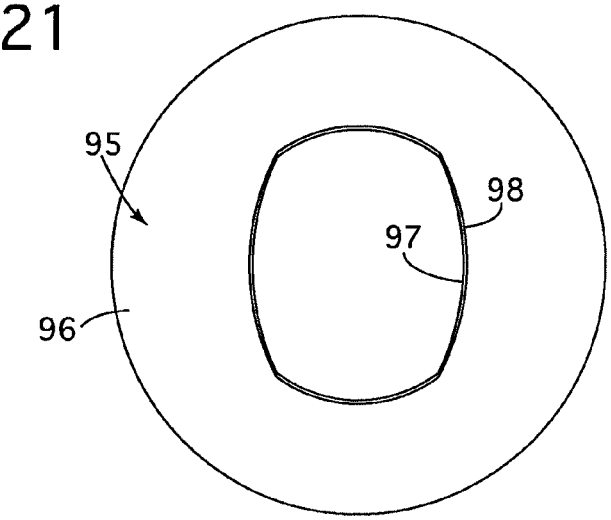
FIG. 21 is a front elevational view of the reinforcing member shown in FIG. 19.

If the lock member 60 of the puncture needle device 90 is moved to the locked position as shown in FIGS. 17 and 18, the stopper portions 62 of the pair of the pair of slide members 61 are positioned immediately in front of (on the ultrasonic endoscope 10 side) opposite ends (upper and lower ends with respect to FIGS. 17 and 18) of the collar 18 even if the collar 18 and the collar receiving hole 92 (the cylindrical connecting body 91) are relatively rotated and positioned at either of the two positions shown in FIGS. 17 and 18. Therefore, not only when the longitudinal direction of the collar 18 and the longitudinal direction of the collar receiving hole 92 are coincident with each other as shown in FIG. 17 but also when the collar 18 and the collar receiving hole 92 relatively rotate to the position shown in FIG. 18, the cylindrical connecting body 91 is prevented from moving in a dismounting direction relative to the pipe sleeve 17 by engagement of the stopper portions 62 of the pair of the pair of slide members 61 with the collar 18, and is further prevented from moving in an inserting direction relative to the pipe sleeve 17 by engagement of the annular flange 19 with the insertion limit surface 37. Accordingly, the cylindrical connecting body 91 is totally prevented from moving relative to the pipe sleeve 17 in the axial direction thereof. Moreover, since the annular flange 19 of the pipe sleeve 17 and the insertion limit surface 37 are brought into surface contact with each other while a peripheral surface of the annular flange 19 and an inner peripheral surface in the anti-tilt recess 35 are brought into surface contact with each other, the cylindrical connecting body 91 is also totally prevented from tilting relative to the pipe sleeve 17.

Although the puncture needle device 90 (the collar receiving hole 92) can rotate slightly relative to the collar 18 even when the lock member 60 moves to the locked position, the operator can manipulate the puncture needle device 90 with precision because the range of rotation of the puncture needle device 90 relative to the collar 18 is extremely narrow.

Although the present invention has been described based on the first through third embodiments of the puncture needle devices, various modifications can be made without departing from the scope of the present invention.

Figure 22:
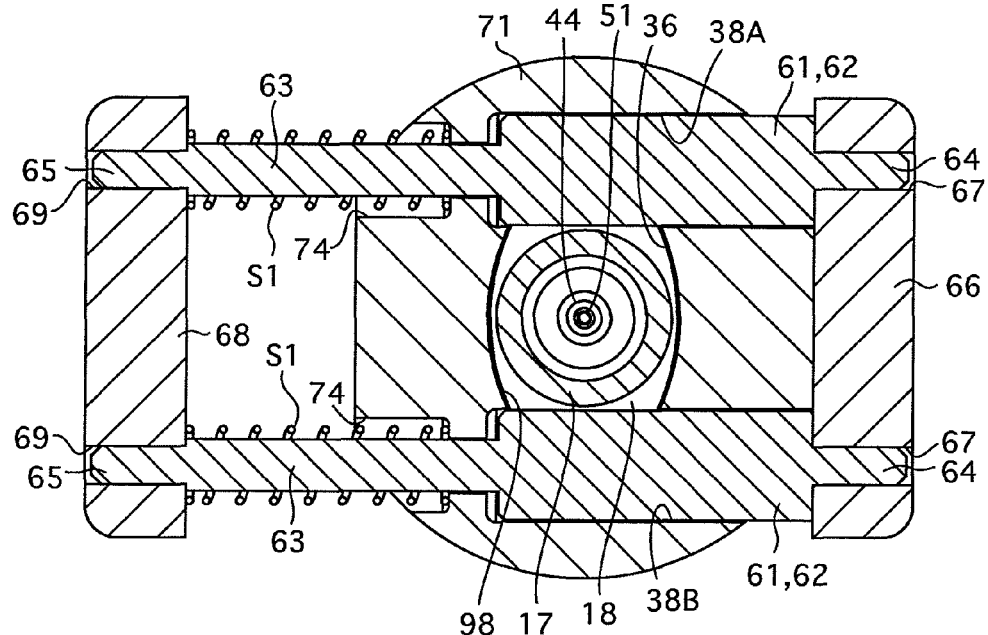
FIG. 22 is a view similar to that of FIG. 8, showing a state where the lock member of the first modified embodiment of the puncture needle device is in the locked position.
Figure 23:
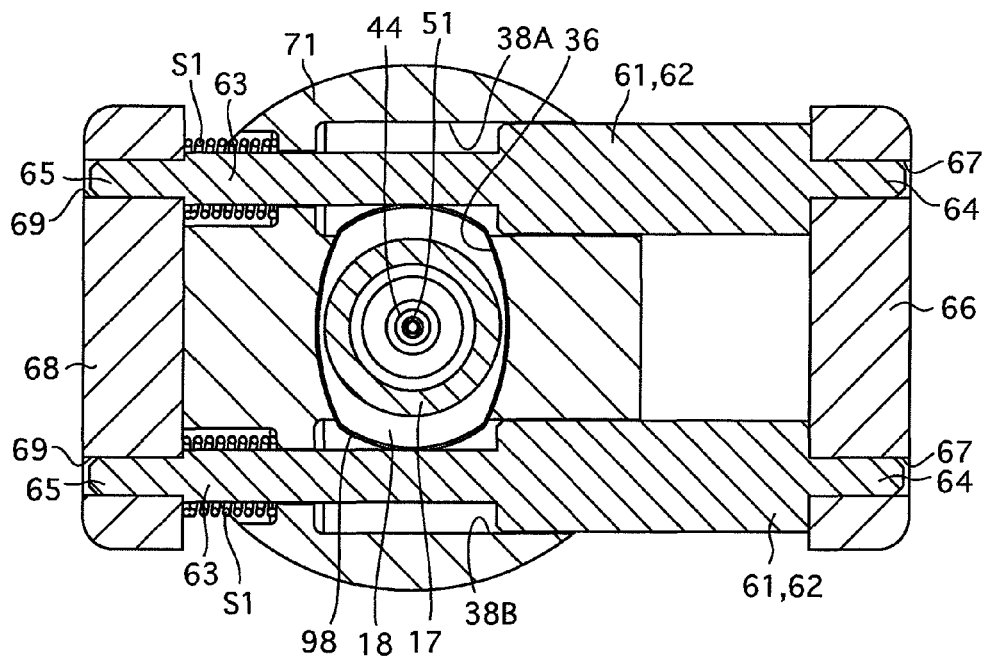
FIG. 23 is a view similar to that of FIG. 9, showing a state where the lock member of the first modified embodiment of the puncture needle device is in the unlocked position.
Figure 24:
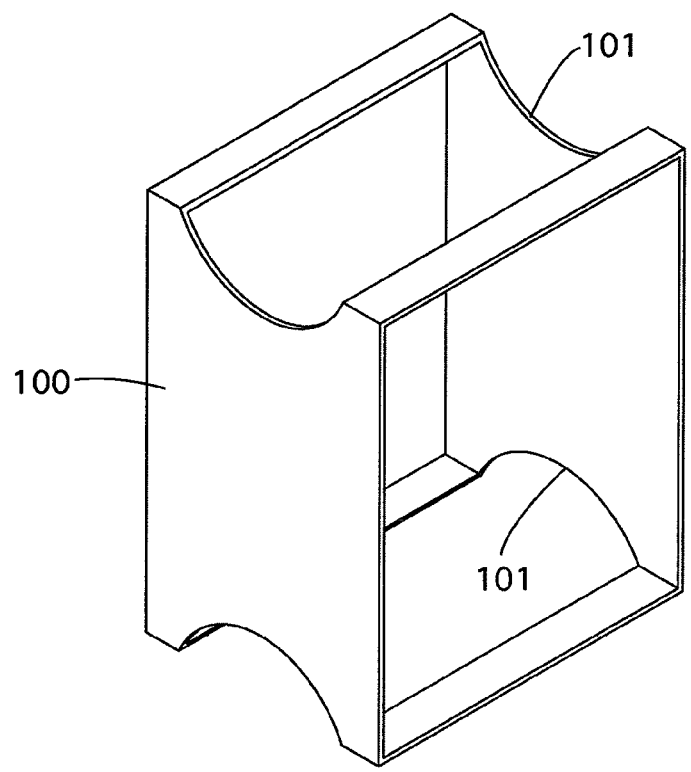
FIG. 24 is a perspective view of a reinforcing member provided as an element of a second modified embodiment of the puncture needle device.
Figure 25:
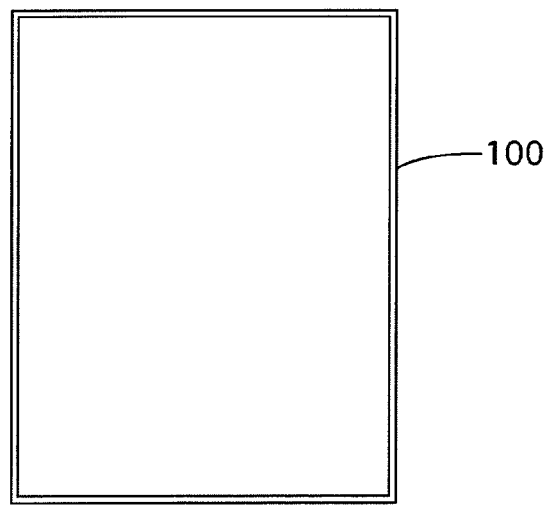
FIG. 25 is a front elevational view of the reinforcing member shown in FIG. 24.
Figure 26:
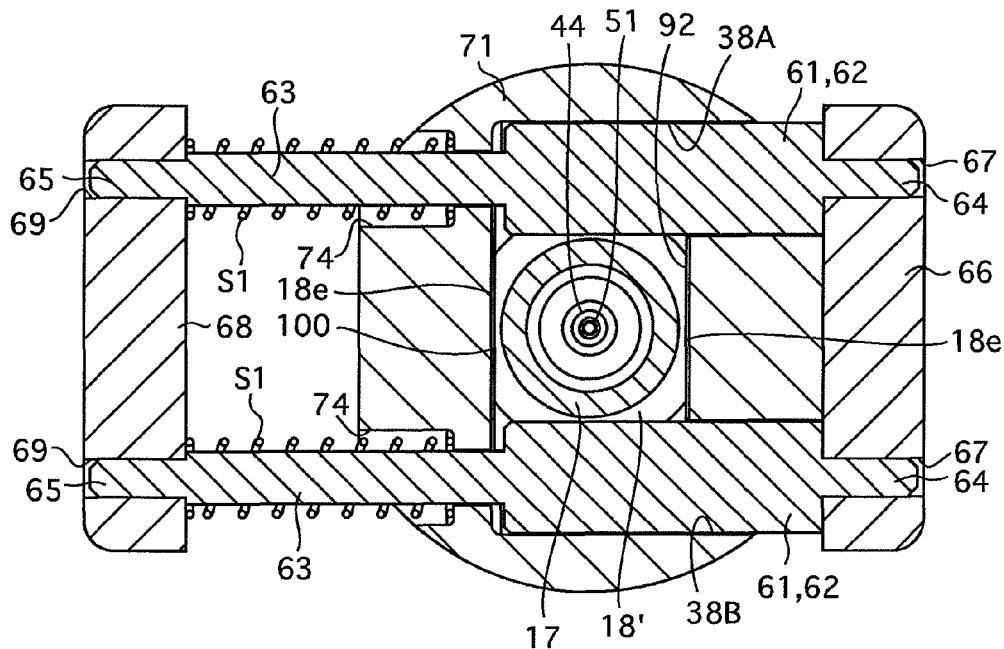
FIG. 26 is a view similar to that of FIG. 8, showing a state where the lock member of the second modified embodiment of the puncture needle device is in the locked position.
Figure 27:
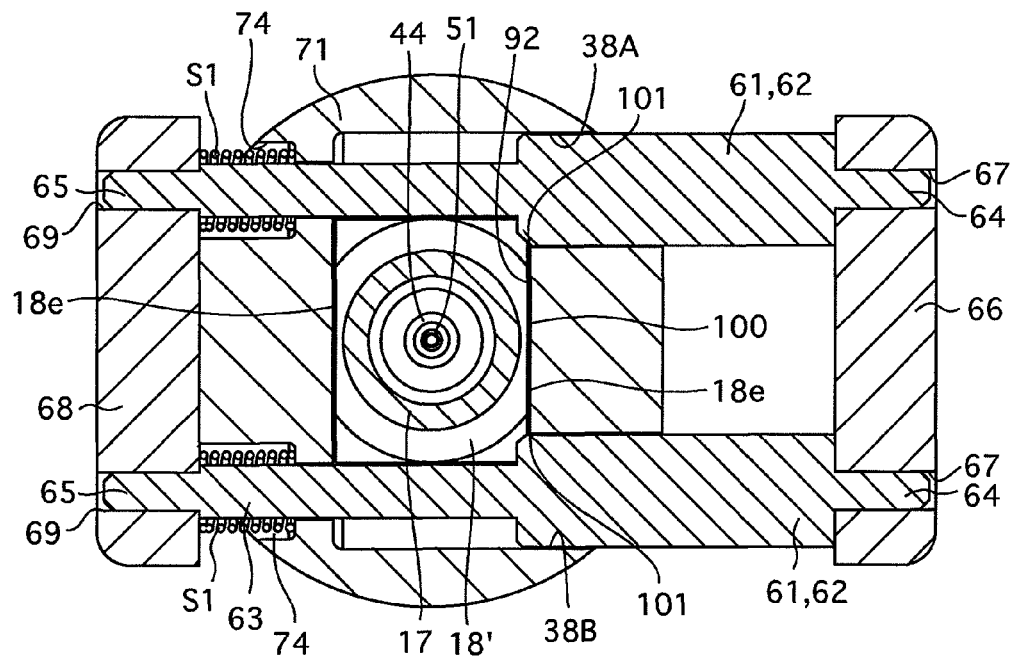
FIG. 27 is a view similar to that of FIG. 9, showing a state where the lock member of the second modified embodiment of the puncture needle device is in the unlocked position.

For instance, as shown in FIGS. 19 through 23, the surfaces in the anti-tilt recess 35 and the collar receiving hole 36 in the second embodiment of the puncture needle device can be covered with a reinforcing member 95 made of stainless steel (JIS SUS304). For instance, the reinforcing member 95 can be formed integrally with the surfaces in the anti-tilt recess 35 and the collar receiving hole 36 by insertion molding. In FIGS. 22 and 23, elements of the puncture needle device which are exactly the same as those in the second embodiment of the puncture needle device 70 and also elements of the puncture needle device which are similar in shape to (i.e., slightly different in shape from) those in the second embodiment of the puncture needle device 70 are designated by the same reference numerals. The reinforcing member 95 is provided with a disk portion 96 and a cylindrical portion 98. The disk portion 96 has the same front elevational shape as the anti-tilt recess 35 and is provided at a center of the disk portion 96 with a through-hole 97 which has substantially in the same cross-sectional shape as that of the collar receiving hole 36. The cylindrical portion 98 projects from a peripheral edge around the through-hole 97 and is substantially identical in cross-sectional shape to the collar receiving hole 36. A pair of side holes (through-holes) 99 are formed through the cylindrical portion 98. The rear surface of the disk portion 96 is in contact with the elastic washer 75 while the outer peripheral surface of the cylindrical portion 98 is in contact with the inner peripheral surface of the collar receiving hole 36. In addition, since the pair of side holes 99 are positioned in the pair of support through-holes 38A and 38B, respectively, and since the stopper portions 62 of the pair of slide members 61 slide through the pair of slide holes 99, respectively, there is no possibility of the stopper portions 62 of the pair of slide members 61 interfering with the cylindrical portion 98.

In this manner, if the surfaces in the anti-tilt recess 35 and the collar receiving hole 36 are provided with (covered with) the reinforcing member 95 that is made of the same material as the pipe sleeve 17, it becomes difficult for wear to occur in the puncture needle device 70 (the reinforcing member 95) even if the collar 18 and the annular flange 19 move while sliding on the reinforcing member 95 when the pipe sleeve 17 is inserted into and removed from the inside of the puncture needle device 70.

The reinforcing member 95 can also be fitted into the anti-tilt recess 35 and the collar receiving hole 36 in the first embodiment of the puncture needle device 30.

Alternatively, as shown in FIGS. 24 through 27, it is possible for the cylindrical connecting body 71 in the modified embodiment shown in FIGS. 19 through 23 to be provided with a collar receiving hole 92 instead of the collar receiving hole 36 and for the surface in the collar receiving hole 92 be covered with a reinforcing member 100 made of stainless steel (JIS SUS304). For instance, the reinforcing member 100 can be formed integrally with the surfaces in the anti-tilt recess 35 and the collar receiving hole 36 by insertion molding. The reinforcing member 100 is in shape of a rectangular hollow-section having the same front elevational shape as that of the collar receiving hole 92 and is provided on opposite side surfaces of the reinforcing member 100 with a pair of side holes (through-holes) 101, respectively, each of which is recessed inwardly to have a semi-circular cylindrical shape as clearly shown in FIG. 24. The outer peripheral surface of the reinforcing member 100 is in contact with the inner surface of the collar receiving hole 92. In addition, since the pair of side holes 101 are positioned in the pair of support through-holes 38A and 38B, respectively, and since the stopper portions 62 of the pair of slide members 61 slide through the pair of slide holes 101, respectively, there is no possibility of the stopper portions 62 of the pair of slide members 61 interfering with the reinforcing member 100.

Furthermore, a collar 18' of the pipe sleeve 17 is non-circular in shape and formed as though radially opposite ends of a circular collar along parallel lines have been cut off, and parallel side edges of the collar 18' thus formed along the aforementioned parallel lines constitute a pair of contact surfaces 18e, respectively. Upon insertion of the collar 18' into the collar receiving hole 92, the pair of contact surfaces 18e come in contact with side surfaces of the collar receiving hole 92, respectively, and a pair of arc-shaped outer edge surfaces of the collar 18' (portions of the outer edge surface of the collar 18' other than the pair of contact surfaces 18e) come in contact with side surfaces of the collar receiving hole 92, which prevents the collar receiving hole 92 from rotating relative to the collar 18'.

In addition, since the surface in the collar receiving hole 92 is provided with (covered with) the reinforcing member 100 that is made of the same material as the pipe sleeve 17, it is difficult for wear to occur in the puncture needle device 70 (the reinforcing member 100) even if the collar 18' moves while sliding on the reinforcing member 100 when the pipe sleeve 17 is inserted into and removed from the inside of the puncture needle device 70.

Each of the pipe sleeve 17 and the reinforcing member 95 or 100 can be made of a metal other than stainless steel (JIS SUS304) (e.g., brass, copper or the like). In this case also, the surface wear of the puncture needle device 30 or 70 due to sliding friction of the pipe sleeve 17 can be reduced (suppressed) compared to a puncture needle device not equipped with the reinforcing member 95 or 100. Furthermore, if each of the pipe sleeve 17 and the reinforcing member 95 or 100 is also made of metal other than stainless steel (JIS SUS304), it is desirable that the metallic material of the reinforcing member 95 or 100 be the same as the metallic material of the pipe sleeve 17.

Moreover, the collar receiving hole 92 of the puncture needle device 90 can also be provided therein with the reinforcing member 100 made of stainless steel (JIS SUS304) or other metallic material.

The shape of the collar 18, which is formed on the pipe sleeve 17, and the shape of the collar receiving hole 36 of the cylindrical connecting body 31 or 71 in the first and second embodiments of the puncture needle devices can be any other shape so long as the shape is non-circular, and the shape of the collar receiving hole 92 in the third embodiment of the puncture needle device can be formed into any other shape so long as such a shape is capable of limiting the range of rotation of the collar receiving hole 92 relative to the pipe sleeve 17 to a predetermined range. Additionally, cross sectional shapes of the reinforcing members 95 and 100 are not limited solely to the above illustrated shapes and can be modified so as to correspond to a cross sectional shape of the associated collar receiving hole.

The annular flange 19 can be replaced by a non-annular-shaped projection or projections which project radially outwards from the outer periphery of the pipe sleeve 17.

Furthermore, the annular flange 19 can be formed at a position closer to the front end opening of the pipe sleeve 17 than the collar 18 or 18'.

Additionally, the control knob 66 or 68 can be formed only on one side of the lock member 60.

A biaser other than the pair of compression coil springs S1 can be used in the second embodiment of the puncture needle device and each of the above described modified embodiments of the puncture needle devices. For instance, a leaf spring or springs, a coned disk spring or springs, or rubber biasing member or members can be used. In addition, it is possible for a ferromagnetic metal to be mounted to a surface of the cylindrical connecting body 71 while at least one of the control knobs 66 and 68 be made of a magnetic material which produces an attractive force between the magnetic material and the ferromagnetic metal which urges the lock member 60 to move toward the locked position.

It is possible that the cylindrical connecting body 31 or 91 in the first and third embodiments of the puncture needle devices and the above described modified embodiments of the puncture needle devices be provided with an annular recess (a female thread) corresponding to the annular recess 72 (the female thread 73) provided therein with an elastic washer and a male-threaded bushing respectively corresponding to the elastic washer 75 and the male-threaded bushing 76.

Obvious changes may be made in the specific embodiments of the present invention described herein, such modifications being within the spirit and scope of the invention claimed. It is indicated that all matter contained herein is illustrative and does not limit the scope of the present invention.

What is claimed is:

1. A puncture needle device detachably attached to an ultrasonic endo scope via a pipe sleeve which projects from said ultrasonic endo scope, said pipe sleeve including a non-circular-shaped collar, said puncture needle device comprising:

a cylindrical connecting body into which said pipe sleeve is inserted when said puncture needle device is attached to said ultrasonic endoscope, said cylindrical connecting body including an insertion limit portion which comes in contact with said pipe sleeve to prevent said pipe sleeve from being further inserted into said cylindrical connecting body when said pipe sleeve is inserted into said cylindrical connecting body to a predetermined position in an internal space of said cylindrical connecting body; and a non-circular-shaped collar receiving hole which is engaged with said collar and irrotatable relative to said collar when said pipe sleeve is inserted into said cylindrical connecting body to said predetermined position;

a flexible sheath which projects outwardly from said cylindrical connecting body through said internal space thereof and is inserted into an internal conduit of said ultrasonic endoscope through the inside of said pipe sleeve when said pipe sleeve is inserted into said internal space of said cylindrical connecting body;

a puncture needle inserted into said sheath to be movable therein; and a lock member supported by said cylindrical connecting body to be movable between an unlocked position that allows said pipe sleeve to be inserted into said cylindrical connecting body to said predetermined position and to be removed from said cylindrical connecting body, and a locked position wherein said lock member contacts said collar of said pipe sleeve, that is inserted into said cylindrical connecting body to said predetermined position, to thereby prevent said collar from moving in a removal direction from said cylindrical connecting body.

2. The puncture needle device according to claim 1, wherein said collar receiving hole and said collar are mutually the same in shape.

3. The puncture needle device according to claim 1, further comprising a biaser, positioned between said lock member and said cylindrical connecting body, for biasing said lock member to move toward said locked position.

4. The puncture needle device according to claim 1, wherein said pipe sleeve comprises a flange which projects from an outer periphery of said pipe sleeve to lie in a plane substantially orthogonal to an axis of said pipe sleeve, wherein said flange is provided closer to a body of said ultrasonic endoscope than said collar and comes into contact with said insertion limit portion when said pipe sleeve is inserted into said cylindrical connecting body to said predetermined position, and wherein said insertion limit portion comprises a surface on said cylindrical connecting body which lies in a plane substantially orthogonal to an axis of said cylindrical connecting body.

5. The puncture needle device according to claim 1, wherein said pipe sleeve comprises a flange which projects from an outer periphery of said pipe sleeve to lie in a plane substantially orthogonal to an axis of said pipe sleeve, wherein said flange is provided closer to a body of said ultrasonic endoscope than said collar and comes into contact with said insertion limit portion when said pipe sleeve is inserted into said cylindrical connecting body to said predetermined position, and wherein said insertion limit portion comprises an elastic member made of an elastic material.

6. The puncture needle device according to claim 4, wherein said flange comprises an annular flange, and wherein said cylindrical connecting body comprises an annular surface with which a periphery of said annular flange comes in contact when said pipe sleeve is inserted into said cylindrical connecting body to said predetermined position.

7. The puncture needle device according to claim 5, wherein said flange comprises an annular flange, and wherein said cylindrical connecting body comprises an annular surface with which a periphery of said annular flange comes in contact when said pipe sleeve is inserted into said cylindrical connecting body to said predetermined position.

8. The puncture needle device according to claim 1, wherein said lock member comprises at least one control knob positioned outside said cylindrical connecting body.

9. The puncture needle device according to claim 8, wherein said lock member extends through said cylindrical connecting body, and wherein two said control knobs are fixed at opposite ends of said lock member, respectively.

10. The puncture needle device according to claim 1, wherein a surface in said collar receiving hole comprises a metal surface.

11. The puncture needle device according to claim 10, wherein said surface in said collar receiving hole and said pipe sleeve are made of a same metallic material.

12. The puncture needle device according to claim 3, wherein said biaser comprises at least one compression spring.

13. The puncture needle device according to claim 5, wherein said elastic member comprises an elastic washer.

14. The puncture needle device according to claim 1, wherein the shape of said collar is defined by a circular collar having radially opposite ends thereof cut off.

* * * * *